(12) United States Patent
Schultheiss et al.

(10) Patent No.: US 8,513,236 B2
(45) Date of Patent: Aug. 20, 2013

(54) PTEROSTILBENE COCRYSTALS

(75) Inventors: Nathan C. Schultheiss, Lafayette, IN (US); Sarah J. Bethune, West Lafayette, IN (US)

(73) Assignee: Laurus Labs Private Limited (IN)

( * ) Notice: Subject to any disclaimer, the term of this patent is extended or adjusted under 35 U.S.C. 154(b) by 381 days.

(21) Appl. No.: 12/847,516

(22) Filed: Jul. 30, 2010

(65) Prior Publication Data

US 2011/0189276 A1 Aug. 4, 2011

Related U.S. Application Data

(60) Provisional application No. 61/301,001, filed on Feb. 3, 2010, provisional application No. 61/301,029, filed on Feb. 3, 2010.

(51) Int. Cl.
*A61P 39/06* (2006.01)
*A61K 31/55* (2006.01)
*C07D 223/18* (2006.01)

(52) U.S. Cl.
USPC .......................................... 514/217; 540/589

(58) Field of Classification Search
USPC ........................................ 514/217; 540/589
See application file for complete search history.

(56) References Cited

U.S. PATENT DOCUMENTS

2009/0006944 A1   1/2009   Dang et al.

FOREIGN PATENT DOCUMENTS

| WO | 2004078163 A2 | 9/2004 |
|---|---|---|
| WO | 2004089313 A2 | 10/2004 |
| WO | 2005117585 A1 | 12/2005 |
| WO | 2008117037 A1 | 10/2008 |
| WO | 2008153945 A2 | 12/2008 |
| WO | WO/2010/141107 A1 | 12/2010 |

OTHER PUBLICATIONS

Lopez-Nicolas, J. M., et al., "Physicochemical Study of the Complexation of Pterostilbene by Natural and Modified Cyclodextrins" Journal of Agricultural and Food Chemistry, 2009, 57, (12), 5294-5300.

Pezet, R., "Purification and characterization of a 32-kDa laccase-like stilbene oxidase produced by *Botrytis cinerea*.", FEMS Micobiology Letters 1998, 167, 203-208.

Jeandet, P. et al., "Characterization of a pterostilbene dehydrodimer produced by laccase of *Botrytis cinerea*." Phytopathology, 1999, 89, (298-302).

Mallavadhani, U. V., et al., "A Highly Reliable Quality-Control Marker for the Ayurvedic Antidiabetic Plant 'Bijasar'." Chromatographia, 2003, 58, 307-312.

Pezet, R. et al., "Method to Determine Resveratrol and Pterostilbene in Grape Berries and Wines using High-Performance Liquid Chromatography and Highly Sensitive Fluorimetric Detection", Journal of Chromatography, 1994, pp. 191-197, vol. 663.

Perecko, T. et al., "Structure-Efficiency Relationship in Derivatives of Stilbene. Comparison of Resveratrol, Pinosylvin and Pterostilbene", Neuroendocrinology Letters, 2008, pp. 802-805, vol. 29, No. 5.

Schultheiss, et al., "Nutraceutical Cocrystals: Utilizing Pterostilbene as a Cocrystal Former", CrystEngComm, 2010, pp. 2436-2442, vol. 12.

*Primary Examiner* — Brenda Coleman
(74) *Attorney, Agent, or Firm* — Blank Rome LLP

(57) ABSTRACT

Cocrystals of pterostilbene are disclosed, including: pterostilbene:caffeine cocrystal, pterostilbene:carbamazepine cocrystal, pterostilbene:glutaric acid cocrystal, and pterostilbene:piperazine cocrystal. The pterostilbene:caffeine cocrystal is polymorphic. Forms I and II of the pterostilbene:caffeine cocrystal are disclosed. The therapeutic uses of the pterostilbene cocrystals and of pharmaceutical/nutraceutical compositions containing them are also disclosed. The disclosure sets out various methods of making and characterizing the pterostilbene cocrystals.

24 Claims, 20 Drawing Sheets

XRPD patterns for pterostilbene Form I, caffeine (as-received), carbamazepine (as-received), cocrystals 1 (Form I and II), and 2 (top to bottom)

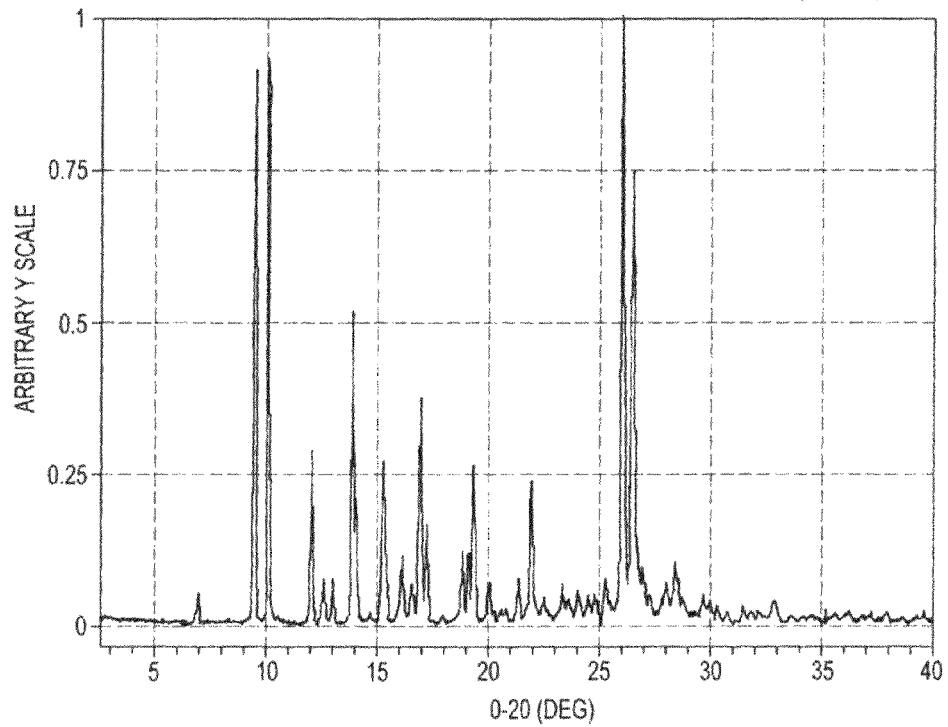
FIG. 2 XRPD PATTERN OF PTEROSTILBENE:CAFFEINE COCRYSTAL 1 (FORM I)
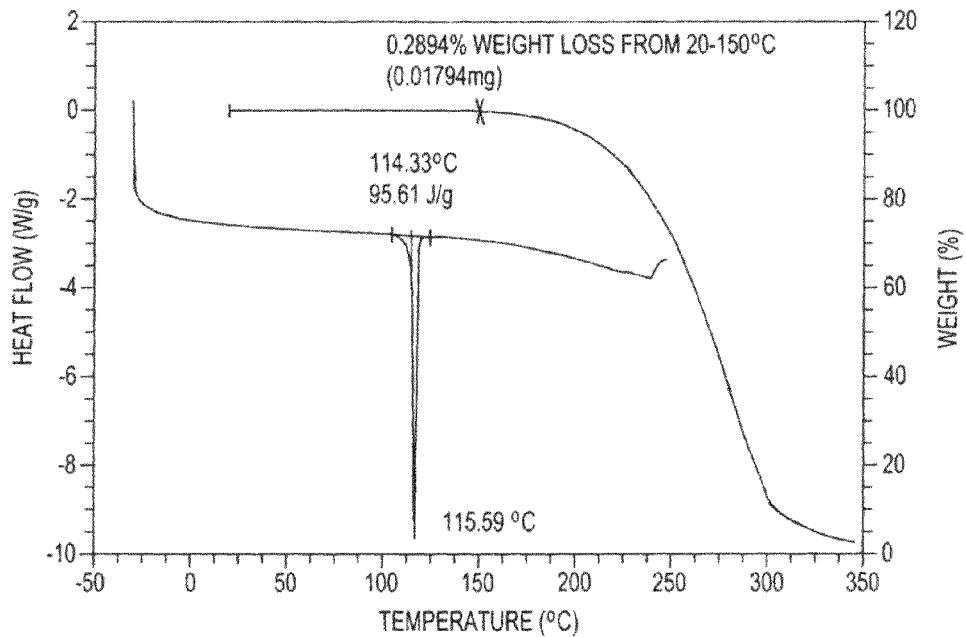
FIG. 3 DSC AND TGA TRACES OF PTEROSTILBENE:CAFFEINE COCRYSTAL 1 (FORM I)

ORTEP drawing of the single-crystal X-ray structure of pterostilbene:caffeine cocrystal 1 (Form I).

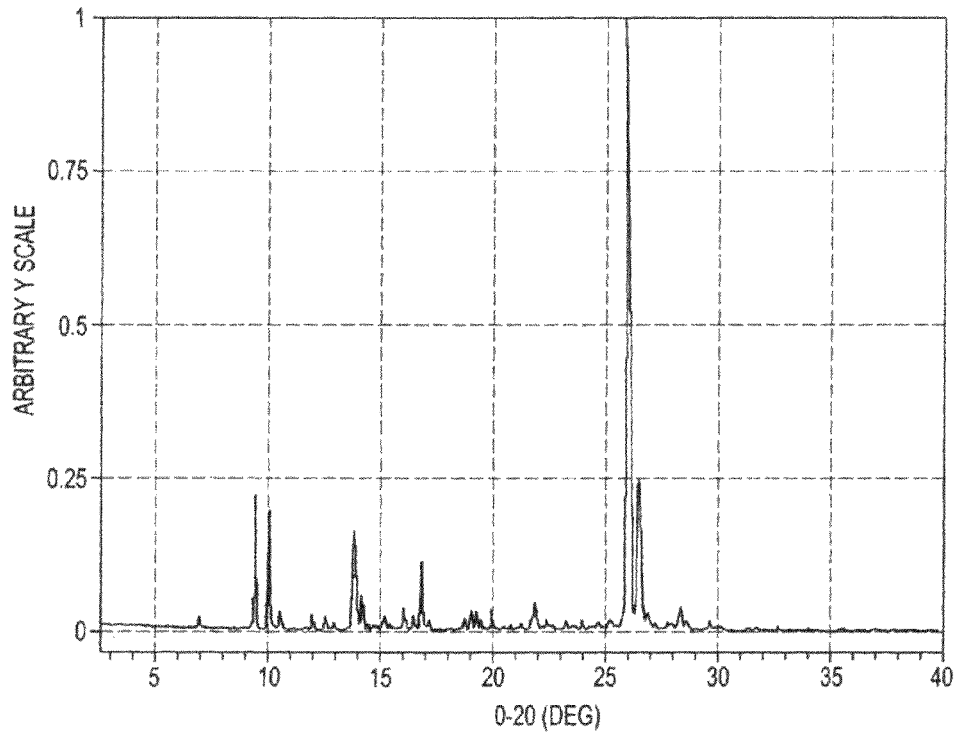
FIG. 6 XRPD PATTERN OF PTEROSTILBENE:CAFFEINE COCRYSTAL 1 (FORM II)
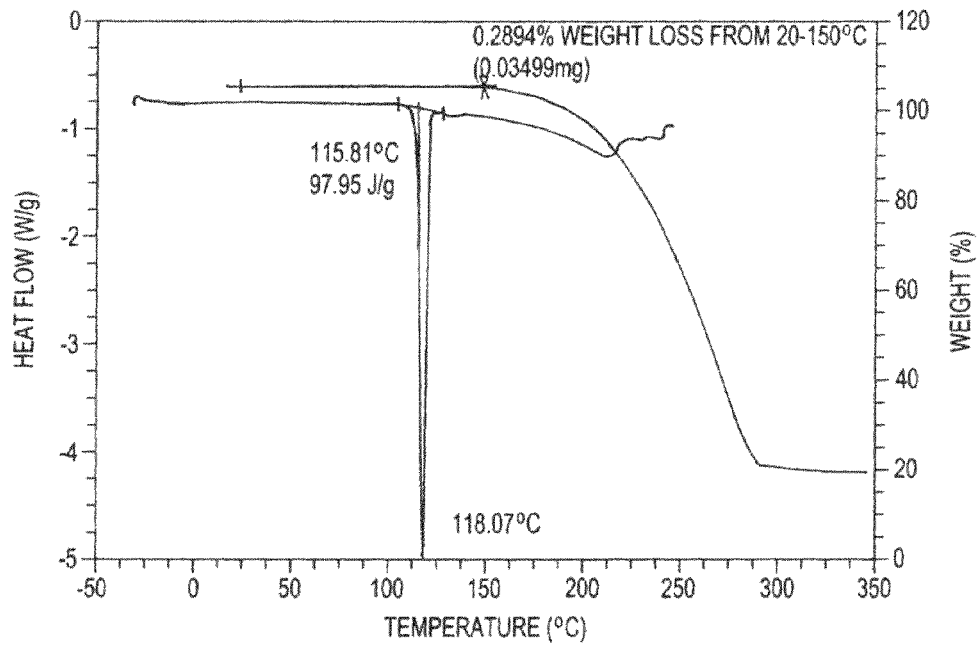
FIG. 7 DSC AND TGA TRACES OF PTEROSTILBENE:CAFFEINE COCRYSTAL 1 (FORM II)

ORTEP drawing of the single-crystal X-ray structure of pterostilbene:caffeine cocrystal 1 (Form II).

XRPD PATTERN OF PTEROSTIBENE:CARBAMAZEPINE COCRYSTAL 2

DSC and TGA traces of pterostilbene:carbamazepine cocrystal 2.

ORTEP drawing of the single-crystal X-ray structure of pterostilbene:carbamazepine cocrystal 2.

XRPD PATTERN OF PTEROSTIBENE:CARBAMAZEPINE COCRYSTAL 3

ORTEP drawing of the single-crystal X-ray structure of pterostilbene:glutaric acid cocrystal 3.

FIG. 15 SOLID STATE $^{13}$C NMR SPECTRUM OF PTEROSTILBENE:GLUTARIC ACID COCRYSTAL 3

FIG. 16 SOLID STATE $^{13}$C NMR SPECTRUM OF PTEROSTIBENE

FIG. 17 SOLID STATE $^{13}$C NMR SPECTRUM OF GLUTARIC ACID

XRPD PATTERN OF PTEROSTIBENE:CARBAMAZEPINE COCRYSTAL 4

DSC and TGA traces of pterostilbene:piperazine cocrystal 4.

ORTEP drawing of the single crystal X-ray structure of pterostilbene:piperazine cocrystal 4.

PTEROSTILBENE COCRYSTALS

CROSS REFERENCE TO RELATED APPLICATIONS

This application is related to and claims priority to U.S. Provisional Application 61/301,001, entitled "Nutraceutical Cocrystals: Utilizing Pterostilbene As A Cocrystal Former," filed Feb. 3, 2010, and U.S. Provisional Application 61/301,029, entitled "Pterostilbene Cocrystals," filed Feb. 3, 2010, the contents of which are incorporated in their entirety herein by reference.

BACKGROUND OF THE INVENTION

1. Field of the Invention

The invention relates to new crystalline compounds containing pterostilbene, more particularly, the invention relates to pterostilbene cocrystals, therapeutic uses of those pterostilbene cocrystals, and pharmaceutical/nutraceutical compositions containing them.

2. Description of Related Art

Pterostilbene (trans-3,5-dimethoxy-4'-hydroxystilbene) is a naturally occurring stilbenoid compound, and a non-ionizable methylated structural analog of resveratrol. The chemical structures of pterostilbene and resveratrol are:

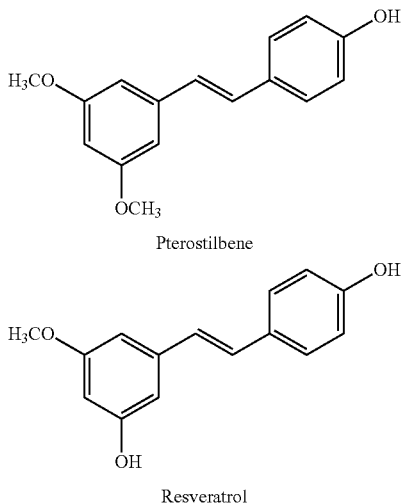

Pterostilbene has been characterized as a nutraceutical, being found in nature in a number of tree barks and a variety of berries, including grapes, as well as plants commonly used in traditional folk medicine. Both resveratrol and pterostilbene have been reported to exhibit a range of biological activities including anti-cancer, antioxidant, anti-inflammatory and other potential health benefits. A number of in vitro and in vivo studies of pterostilbene have been conducted in which it demonstrated cytotoxic activity against cancer cell lines in vitro and decreased plasma glucose levels by 42% in hyperglycemic rats (comparable to the commercially available drug, metformin, which reduces glucose levels by 48%). Additionally, the LDL/HDL cholesterol ratio was significantly lowered in hypercholesterolemic hamsters that were fed 25 ppm pterostilbene in their diet compared to the control animals. The use of pterostilbene to ameliorate oxidative stress and improve working memory and compositions containing pterostilbene are described in published U.S. application 2009/0069444, which is incorporated herein by reference. Significant interest in pterostilbene has therefore been generated in recent years due to its perceived health benefits, leading to increased consumption of foods that contain the compound, such as grapes and berries.

A number of pharmacological studies have been conducted on pterostilbene; but, very little investigation on the behavior of pterostilbene in the solid state has appeared in the open literature, and thus its solid-state properties appear not to have been thoroughly studied to date.

Pterostilbene has been noted to have poor solubility in water, making it difficult to incorporate in food extracts or supplements (Lopez-Nicolas, J. M.; Rodriguez-Bonilla, P.; Mendez-Cazorla, L.; Garcia-Carmona, F., Physicochemical Study of the Complexation of Pterostilbene by Natural and Modified Cyclodextrins. *Journal of Agricultural and Food Chemistry* 2009, 57, (12), 5294-5300.). In addition, pterostilbene exhibits poor bioavailability and is easily oxidized by various enzymes (Pezet, R., Purification and characterization of a 32-kDa laccase-like stilbene oxidase produced by *Botrytis cinerea*. *FEMS Micobiology Letters* 1998, 167, 203-208 and Breuil, A. C.; Jeandet, P.; Adrian, M.; Chopin, F.; Pirio, N.; Meunier, P.; Bessis, R., Characterization of a pterostilbene dehydrodimer produced by laccase of *Botrytis cinerea*. *Phytopathology* 1999, 89, (298-302).). The melting point has been reported as 82° C. (Mallavadhani, U. V.; Sahu, G., Pterostilbene: A Highly Reliable Quality-Control Marker for the Ayurvedic Antidiabetic Plant 'Bijasar'. *Chromatographia* 2003, 58, 307-312.) Efforts to improve the solubility of pterostilbene have focused on formulation approaches such as by using cyclodextrins (Lopez-Nicolas 2009).

Polymorphic forms of pterostilbene have recently been reported. Five polymorphs of pterostilbene are disclosed in PCT/US2010/22285, filed Jan. 27, 2010, which is incorporated herein by reference.

Due to the development of the drug discovery strategy over the last 20 years, physicochemical properties of drug development candidates have changed significantly. The term "drug" as used herein is also meant to include nutraceuticals and active nutraceutical ingredients, even though nutraceuticals are not subject to regulatory trials and approval. The development candidates are generally more lipophilic and less water soluble, which creates huge problems for the industry. Research has shown that some drug candidates fail in the clinical phase due to poor human bioavailability and/or problems with their formulation. Traditional methods to address these problems, without completely redesigning the molecule, include salt selection, producing amorphous material, particle size reduction, prodrugs, and different formulation approaches.

Although therapeutic or clinical efficacy is the primary concern for a drug (or an active nutraceutical ingredient), the salt and solid-state form (i.e., the crystalline or amorphous form) of a drug candidate can be critical to its pharmacological properties and to its development as a viable drug. Crystalline forms of drugs have been used to alter the physicochemical properties of a particular drug. Each crystalline form of a drug candidate can have different solid-state (physical and chemical) properties which may be relevant for drug delivery. Crystalline forms often have better chemical and physical properties than corresponding non-crystalline forms such as the amorphous form. The differences in physical properties exhibited by a novel solid form of a drug (such as a cocrystal or polymorph of the original drug) affect pharmaceutical parameters such as storage stability, compressibility and density (relevant for formulation and product manufacturing), and dissolution rates and solubility (relevant factors in achieving suitable bioavailability).

Dissolution rates of an active ingredient in vivo (e.g., gastric or intestinal fluid) may have therapeutic consequences since it affects the rate at which an orally administered active ingredient may reach the patient's bloodstream. In addition, solubility, a thermodynamic quantity, is a relevant property in evaluating drug delivery because a poorly soluble crystalline form of a drug will deliver less drug than a more soluble one in the same formulation.

Because these practical physical properties are influenced by the solid-state properties of the crystalline form of the drug, they can significantly impact the selection of a compound as a drug, the ultimate pharmaceutical dosage form, the optimization of manufacturing processes, and absorption in the body. Moreover, finding the most adequate solid state form for further drug development can reduce the time and the cost of that development.

Obtaining suitable crystalline forms of a drug is a necessary stage for many orally available drugs. Suitable crystalline forms possess the desired properties of a particular drug. Such suitable crystalline forms may be obtained by forming a cocrystal between the drug and a coformer. Cocrystals often possess more favorable pharmaceutical and pharmacological properties or may be easier to process than known forms of the drug itself. For example, a cocrystal may have different dissolution and solubility properties than the drug. Further, cocrystals may be used as a convenient vehicle for drug delivery, and new drug formulations comprising cocrystals of a given drug may have superior properties, such as solubility, dissolution, hygroscopicity, and storage stability over existing formulations of the drug.

To the best of the joint inventors' knowledge, no cocrystals of pterostilbene have been reported in the open/academic or patent literature. In fact, the field of nutraceutical cocrystals appears to be a relatively unexplored landscape.

A cocrystal of a drug (an active nutraceutical ingredient or an active pharmaceutical ingredient) is a distinct chemical composition between the drug and coformer, and generally possesses distinct crystallographic and spectroscopic properties when compared to those of the drug and coformer individually. Unlike salts, which possess a neutral net charge, but which are comprised of charge-balanced components, cocrystals are comprised of neutral species. Thus, unlike a salt, one cannot determine the stoichiometry of a cocrystal based on charge balance. Indeed, one can often obtain cocrystals having stoichiometric ratios of drug to coformer of greater than or less than 1:1. The stoichiometric ratio of an API to coformer is a generally unpredictable feature of a cocrystal.

Without limiting the present invention to any particular definitional construct because others may define the term differently, the term "cocrystals" may be thought of as multi-component crystals composed of neutral molecules. These multi-component assemblies are continuing to excite and find usefulness, particularly within the pharmaceutical arena, for their ability to alter physicochemical properties. More specifically, cocrystals have been reported to alter aqueous solubility and/or dissolution rates, increase stability with respect to relative humidity, and improve bioavailability of active pharmaceutical ingredients.

A necessary consideration when designing cocrystals, if the end goal is a potential marketed drug-product, is incorporating a suitable cocrystal former (coformer) with an acceptable toxicity profile. Within the pharmaceutical industry, coformers are typically selected from the same list of pharmaceutically accepted salt formers, generally regarded as safe (GRAS) and/or everything added to food in the United States (EAFUS) lists, due to previous occurrence of these molecules in FDA approved drug or food products. An additional group of molecules to be considered as possible coformers are the naturally occurring compounds, nutraceuticals.

A nutraceutical (portmanteau of nutrition and pharmaceutical) compound is defined as, "a food (or part of a food) that provides medical or health benefits, including the prevention and/or treatment of a disease and possesses a physiological benefit or reduces the risk of chronic disease". Utilizing naturally occurring compounds as coformers gives extension to the list of potential molecules accessible to the pharmaceutical industry and provides additional physiological benefits to the consumer.

In some circumstances, such as with cocrystals of carboxylic acids, the coformer is generally viewed as the acid moiety whereas the compound whose therapeutic properties are of interest is viewed as the drug, as in the case of the pterostilbene:glutaric acid cocrystal. In other circumstances, more than one component may be viewed as the drug. In the case of the pterostilbene cocrystals reported herein, one may view pterostilbene as acting as a drug and carbamazepine as a coformer or the reverse. Likewise, one may view the pterostilbene in the pterostilbene:caffeine cocrystal as a drug and the caffeine as a coformer or the reverse. However, regardless of what label is used for a particular component, the cocrystal structure is not altered. For purposes of the invention reported herein, pterostilbene is viewed as the drug whereas the second component of each of the cocrystals is viewed as the coformer.

In a cocrystal, the drug and the coformers each possess unique lattice positions within the unit cell of the crystal lattice. Crystallographic and spectroscopic properties of cocrystals can be analyzed as with other crystalline forms such as with X-ray powder diffraction (XRPD), single crystal X-ray crystallography, and solid state NMR, among other techniques. Cocrystals often also exhibit distinct thermal behavior compared with other forms of the corresponding drug. Thermal behavior may be analyzed by such techniques as capillary melting point, thermogravimetric analysis (TGA), and differential scanning calorimetry (DSC) to name a few. These techniques can be used to identify and characterize the cocrystals.

SUMMARY OF THE INVENTION

The present invention relates to the following novel pterostilbene cocrystals:

(1) pterostilbene:caffeine ("cocrystal 1");

(2) pterostilbene:carbamazepine ("cocrystal 2");

(3) pterostilbene:glutaric acid ("cocrystal 3"); and (4) pterostilbene:piperazine ("cocrystal 4").

The molecular structures of pterostilbene, caffeine, carbamazepine, glutaric acid, and piperazine (left-to-right) are shown below:

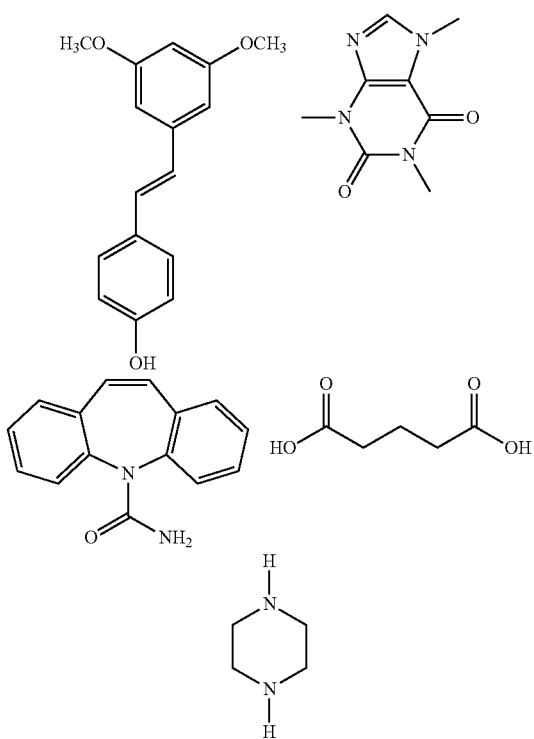

For each cocrystal, the single crystal structures were determined and several physical properties were measured.

The pterostilbene:caffeine cocrystal is polymorphic.

Cocrystals were prepared having a 1:1 stoichiometric molar ratio of pterostilbene with caffeine (two polymorphs, Form I and Form II).

Cocrystals were prepared and characterized by crystallographic (XRPD, single-crystal) and thermoanalytical (TGA, DSC) techniques, among others.

Physical stability of the cocrystals with respect to relative humidity (RH) was examined and found to be dramatically improved, in some cases, in relationship to, for example, caffeine or carbamazepine.

The pterostilbene:carbamazepine cocrystal was stable upon slurrying in water for three days; therefore, aqueous equilibrium solubility measurements were carried out, revealing that the cocrystal solubility was 7× lower than carbamazepine dihydrate and 2.5× lower than pterostilbene.

Slurring the pterostilbene:caffeine cocrystal Form I in water led to a solution that was supersaturated with respect to pterostilbene, resulting in the precipitation of pterostilbene after three days; therefore concentrations at specific time points were measured as opposed to equilibrium solubility. At five hours the concentration of the caffeine cocrystal was 33× lower than the caffeine hydrate solubility, but was 27× higher than the pterostilbene solubility.

Slurring the pterostilbene:piperazine cocrystal in water led to a solution that was supersaturated with respect to pterostilbene, resulting in the precipitation of pterostilbene after three days; therefore concentrations at specific time points were measured. At five hours the concentration of the pterostilbene:piperazine cocrystal revealed a 6× increase in comparison to the solubility of pterostilbene.

Other properties of the cocrystals were also characterized.

As noted above, the present invention also relates to Forms I and II of the pterostilbene:caffeine cocrystal 1.

The invention further relates to therapeutic uses of those pterostilbene cocrystals, and pharmaceutical/nutraceutical compositions containing them.

Methods of making the pterostilbene cocrystals are a further aspect of the invention.

BRIEF DESCRIPTION OF THE FIGURES

FIG. 2 shows the XRPD pattern of pterostilbene:caffeine cocrystal 1 (Form I).

FIG. 3 shows the DSC and TGA traces of pterostilbene:caffeine cocrystal 1 (Form I).

FIG. 6 shows the XRPD pattern of pterostilbene:caffeine cocrystal 1 (Form II).

FIG. 7 shows the DSC and TGA traces of pterostilbene:caffeine cocrystal 1 (Form II).

DETAILED DESCRIPTION OF THE INVENTION

Figure 1:
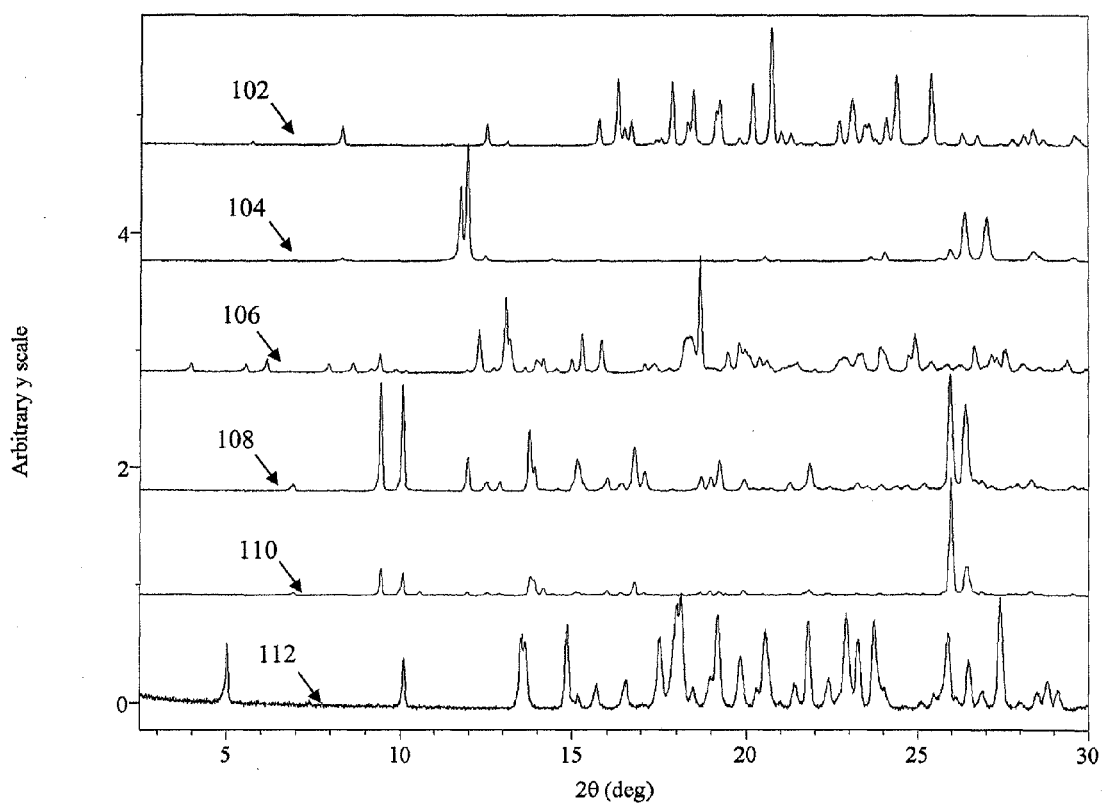
FIG. 1 shows juxtaposed XRPD patterns for pterostilbene (Form I), caffeine, carbamazepine, a cocrystals 1 (Form I and II) and 2.

Several preferred embodiments of the present invention are described for illustrative purposes, it being understood that the invention may be embodied in other forms not specifically shown in the drawing or described below.

The invention relates to novel pterostilbene cocrystals: pterostilbene:caffeine cocrystal 1, pterostilbene:carbamazepine cocrystal 2, pterostilbene:glutaric acid cocrystal 3, and pterostilbene:piperazine cocrystal 4. The pterostilbene:caffeine cocrystal is polymorphic. The invention also relates to Forms I and II of the pterostilbene:caffeine cocrystal 1. Cocrystals 1, 2, and 3 have a 1:1 molar ratio of pterostilbene to the respective coformer, while 4 has a 2:1 molar ratio. The preparation and characterization of each cocrystal is described in the examples below.

Other embodiments of the invention include compositions containing one or more solid forms of the pterostilbene cocrystals such as pharmaceutical or nutraceutical dosage forms. Such pharmaceutical dosage forms may include one or more excipients, including, without limitation, binders, fillers, lubricants, emulsifiers, suspending agents, sweeteners, flavorings, preservatives, buffers, wetting agents, disintegrants, effervescent agents, and other conventional excipients and additives. The compositions of the invention can thus include any one or a combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to humans without causing deleterious side effects or interactions.

Suitable additives may include, but are not limited to, microcrystalline cellulose, lactose, sucrose, fructose, glucose, dextrose, other sugars, di-basic calcium phosphate, calcium sulfate, cellulose, methylcellulose, cellulose derivatives, kaolin, mannitol, lactitol, maltitol, xylitol, sorbitol, other sugar alcohols, dry starch, dextrin, maltodextrin, other polysaccharides, or mixtures thereof.

In one embodiment of the present invention the solid-state pterostilbene cocrystal dosage is an oral dosage form. Exemplary oral dosage forms for use in the present disclosure include tablets, capsules, powders, suspensions, and lozenges, which may be prepared by any conventional method of preparing pharmaceutical oral dosage forms. Oral dosage forms, such as tablets, may contain one or more of the conventional, pharmaceutically acceptable additional formulation ingredients, including but not limited to, release modifying agents, glidants, compression aides, disintegrants, effervescent agents, lubricants, binders, diluents, flavors, flavor enhancers, sweeteners, and preservatives. Tablet dosage forms may be partially or fully coated, sub-coated, uncoated, and may include channeling agents. The ingredients are selected from a wide variety of excipients known in the pharmaceutical formulation art. Depending on the desired properties of the oral dosage form, any number of ingredients may be selected alone or in combination for their known use in preparing such dosage forms as tablets.

Pterostilbene, an antioxidant, is known to be beneficial for human health. The invention also provides therapeutic uses of the pterostilbene cocrystals and methods for delivering them, and dosage forms containing them, to humans. The dosage forms may be administered using any amount, any form of pharmaceutical composition and any route of administration effective for the treatment. After formulation with an appropriate pharmaceutically acceptable carrier in a desired dosage, as known by those of skill in the art, the pharmaceutical compositions of this disclosure can be administered to humans and other animals orally, rectally, parenterally, intravenously, intracisternally, intravaginally, intraperitoneally, topically (as by powders, ointments, or drops), bucally, as an oral or nasal spray, or the like, depending on the location and severity of the condition being treated. In one embodiment of the disclosure, the method of delivery is with an oral dosage form.

In certain embodiments, solid forms containing a pterostilbene cocrystal of the invention may be administered at pterostilbene dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired effect. It will also be appreciated that dosages smaller than 0.001 mg/kg or greater than 50 mg/kg (for example 50-100 mg/kg) can be administered to a subject in need thereof.

Coformers that may be used with pterostilbene according to the present invention may include, but are not limited to, any one or more of the following active pharmaceutical ingredients: analgesic and anti-inflammatory drugs (NSAIDs, fentanyl, indomethacin, ibuprofen, ketoprofen, nabumetone, paracetamol, piroxicam, tramadol, COX-2 inhibitors such as celecoxib and rofecoxib); anti-arrhythmic drugs (procainamide, quinidine, verapamil); antibacterial and antiprotozoal agents (amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethamine-sulfadoxime, streptomycin); anticoagulants (warfarin); antidepressants (amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline; 3-[2-[3,4-dihydrobenzofuro[3,2-c]pyridin-2(1H)-yl]ethyl]-2-methyl-4H-pyrido[1,2-a]pyrimidin-4-one); anti-diabetic drugs (glibenclamide, metformin); anti-epileptic drugs (carbamazepine, clonazepam, ethosuximide, gabapentin, lamotrigine, levetiracetam, phenobarbitone, phenytoin, primidone, tiagabine, topiramate, valpromide, vigabatrin); antifungal agents (amphotericin, clotrimazole, econazole, fluconazole, flucytosine, griseofulvin, itraconazole, ketoconazole, miconazole nitrate, nystatin, terbinafine, voriconazole); antihistamines (astemizole, cinnarizine, cyproheptadine, decarboethoxyloratadine, fexofenadine, flunarizine, levocabastine, loratadine, norastemizole, oxatomide, promethazine, terfenadine); anti-hypertensive drugs (captopril, enalapril, ketanserin, lisinopril, minoxidil, prazosin, ramipril, reserpine, terazosin); anti-muscarinic agents (atropine sulphate, hyoscine); antineoplastic agents and antimetabolites (platinum compounds, such as cisplatin, carboplatin; taxanes, such as paclitaxel, docetaxel; tecans, such as camptothecin, irinotecan, topotecan; vinca alkaloids, such as vinblastine, vindecine, vincristine, vinorelbine; nucleoside derivatives and folic acid antagonists such as 5-fluorouracil, capecitabine, gemcitabine, mercaptopurine, thioguanine, cladribine, methotrexate; alkylating agents, such as the nitrogen mustards, e.g., cyclophosphamide, chlorambucil, chiormethine, iphosphamide, melphalan, or the nitrosoureas, e.g., carmustine, lomustine, or other alkylating agents, e.g., busulphan, dacarbazine, procarbazine, thiotepa; antibiotics, such as daunorubicin, doxorubicin, idarubicin, epirubicin, bleomycin, dactinomycin, mitomycin; HER 2antibody, such as trastuzumab; podophyllotoxin derivatives, such as etoposide, teniposide; famesyl transferase inhibitors; anthrachinon derivatives, such as mitoxantron); anti-migraine drugs (alniditan, naratriptan, sumatriptan); anti-Parkinsonian drugs (bromocryptine mesylate, levodopa, selegiline); antipsychotic, hypnotic, and sedating agents (alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone, zolpidem); anti-stroke agents (lubeluzole, lubeluzole oxide, riluzole, aptiganel, eliprodil, remacemide); antitussive (dextromethorphan, levodropropizine); antivirals (acyclovir, ganciclovir, loviride, tivirapine, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea); beta-adrenoceptor blocking agents (atenolol, carvedilol, metoprolol, nebivolol, propanolol); cardiac inotropic agents (amrinone, digitoxin, digoxin, milrinone); corticosteroids (beclomethasone dipropionate, betamethasone, budesonide, dexamethasone, hydrocortisone, methylprednisolone, prednisolone, prednisone, triamcinolone); disinfectants (chlorhexidine); diuretics (acetazolamide, frusemide, hydrochlorothiazide, isosorbide); enzymes; essential oils (anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme); gastro-intestinal agents (cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, sulphasalazine); haemostatics (aminocaproic acid); lipid regulating agents (atorvastatin, lovastatin, pravastatin, probucol, simvastatin); local anaesthetics (benzocaine, lignocaine); opioid analgesics (buprenorphine, codeine, dextromoramide, dihydrocodeine, hydrocodone, oxycodone, morphine); parasympathomimetics and anti-dementia drugs (AIT-082, eptastigmine, galanthamine, metrifonate, milameline, neostigmine, physostigmine, tacrine, donepezil, rivastigmine, sabcomeline, talsaclidine, xanomeline, memantine, lazabemide); peptides and proteins (antibodies, becaplermin, cyclosporine, erythropoietin, immunoglobulins, insuline); sex hormones (oestrogens, conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone, quingestanol acetate); stimulating agents (sildenafil); vasodilators (amlodipine, buflomedil, amyl nitrite, diltiazem, dipyridamole, glyceryl trinitrate, isosorbide dinitrate, lidoflazine, molsidomine, nicardipine, nifedipine, oxpentifylline, pentaerythritol tetranitrate); their N-oxides, their pharmaceutically acceptable acid or base addition salts and their stereochemically isomeric forms.

The following are non-limiting examples.

EXAMPLES

Preparation of Pterostilbene Cocrystals

Reagents: Pterostilbene was acquired from Aptuit Laurus Pty. Ltd., India. Caffeine, carbamazepine, glutaric acid, and piperazine were purchased from Sigma-Aldrich and used as received. All other chemicals were purchased from various suppliers and used without further purification. FIG. 1 shows XRPD patterns for pterostilbene Form I (102), caffeine (as-received) (104), carbamazepine (as-received) (106), and cocrystals 1 (Form I and II) and 2 (top to bottom) (108, 110, 112).

Techniques: The following techniques were used to prepare the pterostilbene cocrystals of the invention. Of the techniques described below, generally speaking, grinding method was used for determining cocrystal formation, while solvent based methods at ambient or elevated temperatures were used for scale-up and characterization, and vapor diffusion or slow evaporation was used to grow single crystals.

Grinding Method: A weighed amount of pterostilbene as the active pharmaceutical/nutraceutical ingredient (API) was transferred to a milling container (typically, agate). A coformer was added in 1:1 or 2:1 (API:coformer) molar ratio. A small amount of solvent which may include non-polar, polar aprotic, or polar aprotic (if specified) and an agate milling ball were added to the container, which was then attached to a Retsch mill. The mixture was milled for approximately 20 minutes at 30 Hz, although other pre-determined time periods and other frequencies are also contemplated. Where noted, solids were scraped down sides of jar halfway through the milling process. The resulting solids were transferred to a clean vial and analyzed.

Solvent Based Method at Ambient Temperature: A mixture of pterostilbene and a coformer was prepared in a given solvent by adding solids of one component to a saturated (or near saturated) solution of the other component. The solution was allowed to stir for an extended pre-determined period of time. Any precipitated solids were isolated and analyzed.

Solvent Based Method at Elevated Temperature: A solution of pterostilbene and a coformer (in 1:1 or 2:1 API: coformer molar ratio) was prepared in a solvent or a solvent system with heating such that the mixture is heated above ambient or room temperature. In some cases, solutions were filtered through a 0.2-µm nylon filter prior to cooling. Upon cooling to ambient temperature, solids were formed. The solids were isolated and analyzed if specified. In some cases where sticky films resulted, the film was redissolved in a different solvent and the experiment was repeated or other techniques were employed.

Vapor Diffusion: A concentrated solution of pterostilbene and a coformer (in 1:1 API: coformer molar ratio) was prepared in a solvent. The solution was dispensed into a small container, which was then placed inside a larger vessel containing antisolvent, which could include, but is not limited to, water. The small container was left uncapped and the larger vessel was capped for a period of time to allow vapor diffusion to occur. Solids were isolated and analyzed, if indicated.

Slow Evaporation: A solution of pterostilbene and a coformer (in 1:1 or 2:1 API:coformer molar ratio) was prepared in a solvent or solvent system with agitation and/or gentle heating. The solution was allowed to evaporate at ambient conditions in a loosely covered vial. In some cases, solutions were filtered through a 0.2-µm nylon filter prior to evaporation. The solids were isolated and analyzed if specified.

Abbreviations: The following abbreviations are used in the examples below:

EtOH ethanol

IPA isopropanol

EtOAc ethyl acetate

Example 1

Preparation of 1:1 Pterostilbene:Caffeine Cocrystal, 1 (Form I)

Cocrystal 1 (Form 1) was prepared by a grinding method and solvent-based methods. For grinding, a 1:1 mixture of pterostilbene (~45 mg, ~0.18 mmol) and caffeine (~34 mg, ~0.18 mmol) were added to a milling jar. Approximately 25 μL, of solvent (chloroform, acetonitrile, ethanol, or nitromethane) were added and the material was ground for 20 minutes at a rate of 30 Hz. For the solvent-based methods at ambient temperature, solid caffeine was added to a nearly saturated solution of pterostilbene in ethanol and allowed to stir for ~24 hours before filtering. Single crystals were grown from a vapor diffusion experiment where a 1:1 mixture of pterostilbene (56.0 mg, 0.22 mmol) and caffeine (42.4 mg, 0.22 mmol) was dissolved in a minimal amount of methanol (2 ml) in a 1 dram vial. The 1 dram vial was placed uncapped in a 20 ml vial containing water. The larger vial was capped, and after 2 days, rod-shaped crystals were harvested.

Example 2

Preparation of 1:1 Pterostilbene:Caffeine Cocrystal, 1 (Form II)

Single crystals were grown from a vapor diffusion experiment where a 1:1 mixture of pterostilbene (~56.0 mg, ~0.22 mmol) and caffeine (~42.0 mg, ~0.22 mmol) was dissolved in a minimal amount of methanol (2 ml) in a 1 dram vial. The 1 dram vial was placed uncapped in a 20 ml vial containing water. The larger vial was capped, and after 2 days colorless, prism-shaped crystals were harvested.

Example 3

Preparation of 1:1 Pterostilbene:Carbamazepine Cocrystal, 2

Cocrystal 2 was prepared by a grinding method and solvent-based methods. For grinding, a 1:1 mixture of pterostilbene (~41 mg, ~0.16 mmol) and carbamazepine (~38 mg, ~0.16 mmol) was added to a milling jar. Approximately 25 μL, of solvent (chloroform, acetonitrile, ethanol, or p-dioxane) were added and the material was ground for 20 minutes at a rate of 30 Hz. The cocrystal was scaled up using solvent-based methods at ambient temperature, where solid carbamazepine was added to a nearly saturated solution of pterostilbene in toluene and allowed to stir for ~24 hours before filtering. Single crystals were grown from a vapor diffusion experiment where a 1:1 mixture of pterostilbene (55.3 mg, 0.22 mmol) and carbamazepine (50.8 mg, 0.22 mmol) was dissolved in a minimal amount of methanol (2 ml) in a 1 dram vial. The 1 dram vial was placed uncapped in a 20 ml vial containing water. The larger vial was capped, and after 2 days, rod-shaped crystals were harvested.

Example 4

Preparation of 1:1 Pterostilbene:Glutaric Acid Cocrystal, 3

Pterostilbene:glutaric acid cocrystals were prepared by a grinding method, slow evaporation, or slow cooling. Utilizing grinding conditions, a 1:1 mixture of pterostilbene (~36 mg, ~0.14 mmol) and glutaric acid (~19 mg, ~0.14 mmol) was added to an agate milling jar. Approximately 10 μL of solvent (toluene or 2-propanol) were added and the material ground for 20 minutes at a rate of 30 Hz. Using a solvent-based method at elevated temperature, the cocrystal was scaled up by dissolving a mixture of pterostilbene (3.03 g, 11.8 mmol) and glutaric acid (1.55 g, 11.7 mmol) in toluene (~40 mL) with heat and allowing the solution to slowly cool. The homogeneous solution was stirred, and, upon cooling, the solids precipitated. The white, crystalline solid was filtered and dried yielding 3.79 g, 83%. Single crystals were grown from slowly evaporating a 1:1 mixture of pterostilbene (25.0 mg, 0.10 mmol) and glutaric acid (13.1 mg, 0.10 mmol) in toluene (3 mL). After 1 day plate-shaped crystals were harvested.

Example 5

Preparation of Pterostilbene:Piperazine Cocrystal, 4

Pterostilbene: piperazine cocrystals were prepared by a grinding method, slow evaporation, or slow cooling. For grinding conditions, a 2:1 mixture of pterostilbene (~65 mg, ~0.25 mmol) and piperazine (~11 mg, ~0.13 mmol) were added to an agate mill. Approximately 10 μL, of solvent (ethanol or nitromethane) were added and the material ground for 20 minutes at a rate of 30 Hz. Using a solvent-based method at elevated temperature, the cocrystal was scaled up by dissolving a mixture of pterostilbene (5.12 g, 20.0 mmol) and piperazine (862 mg, 10.0 mmol) in ethanol (~70 mL) with heat. The solution was stirred in an oil bath for approximately 1 h, upon which the heat was removed and solids precipitated. The white, crystalline solid was filtered and dried, yielding 10.54 g, 88%. Single crystals of cocrystal 4 were grown from slowly evaporating a 1:1 mixture of pterostilbene (135.2 mg, 0.53 mmol) and piperazine (45.5 mg, 0.53 mmol) in ethanol (2 mL). After 1 day rod-shaped crystals were harvested.

Characterization of Pterostilbene Cocrystals

Characterization Methods: The pterostilbene cocrystals of the present invention were characterized by X-ray powder diffraction, thermal gravimetric analysis, differential scanning calorimetry, single crystal X-ray diffraction, and solid state $^{13}C$ NMR. Each method used is described below. The stability (with respect to relative humidity) and solubility of the pterostilbene cocrystals were also determined as described below.

As used herein, the word "characterize" means to identify a collection of data which may be used to identify a cocrystal of the invention. The process by which cocrystals are characterized involves analyzing data collected on the cocrystals so as to allow one of ordinary skill in the art to distinguish cocrystals of the same active pharmaceutical or nutraceutical ingredient. Chemical identity of cocrystals can often be determined with solution-state techniques such as $^1H$ NMR spectroscopy which will provide or assist in providing the chemical identity of the coformers as well as the API or active nutraceutical ingredient. Thus, such techniques can be used to differentiate and characterize cocrystals having different coformers but the same drug (or active nutraceutical ingredient).

One may also, for example, collect X-ray powder diffraction data on cocrystals such as cocrystals of pterostilbene. An X-ray powder diffraction plot is an x-y graph with °2θ (diffraction angle) on the x-axis and intensity on the y-axis. The peaks within this plot may be used to characterize a crystalline solid form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the art to characterize solid forms such as cocrystals. Indeed, those of ordinary skill in the art attempt to choose peaks which appear to be less influenced by preferred orientation to so as to make characterization more robust.

As with any data measurement, there is variability in X-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts X-rays. Another source of variability comes from instrument parameters. Different X-ray instruments operate using different parameters and these may lead to slightly different diffraction patterns from the same crystalline solid form. Likewise, different software packages process X-ray data differently and this also leads to variability. These and other sources of variability are known to those of ordinary skill in the pharmaceutical arts.

Due to such sources of variability, it is common to recite X-ray diffraction peaks using the word "about" prior to the peak value in °2θ which presents the data to within 0.1 or 0.2 °2θ of the stated peak value depending on the circumstances. The X-ray powder diffraction data corresponding to the cocrystals of pterostilbene of the disclosure were collected on instruments which were routinely calibrated and operated by skilled scientists. Accordingly, the variability associated with these data would be expected to be closer to ±0.1 °2θ and are so reported herein.

For each cocrystal disclosed herein, peak lists for the XRPD patterns are presented in tabular form. Additionally, a subset of those peak lists was generated and identified as "representative" peaks. Representative peaks are selected from the generated peak list on the entire pattern by identifying peaks that are generally non-overlapping, at low angle, with relatively strong intensity, and for which assessments of the affects of preferred orientation and particle statistics on the peaks have been made.

For each of the cocrystals of pterostilbene of the invention, peak lists of the XRPD patterns as well as representative peaks were identified. For each cocrystal, characterization may be made by utilizing any one of the corresponding representative peaks, a collection of more than one of the peaks up to and including the entire representative peak list for each cocrystal. Further, although not necessary to characterize a particular cocrystal of pterostilbene, one may select the entire diffraction pattern to characterize the cocrystal.

X-ray Powder Diffraction (XRPD). Patterns were collected using a PANalytical X'Pert Pro or Inel XRG-3000 diffractometer. An incident beam of Cu Kα radiation was produced using an Optix long, fine-focus source. PANalytical data were collected and analysed using X'Pert Pro Data Collector software (v. 2.2b). Prior to the analysis, a silicon specimen (NIST SRM 640c) was analyzed to verify the Si 111 peak position. PANalytical diffraction patterns were collected using a scanning position-sensitive detector (X'Celerator) located 240 mm from the specimen.

Thermogravimetric Analysis (TGA). Thermogravimetric analyses were performed using a TA Instruments 2050 thermogravimetric analyzer. The sample was placed in an aluminum sample pan and inserted into the TG furnace. Analysis began at ~20° C., and the furnace was heated under nitrogen at a rate of 10 K/min, up to a final temperature of 350° C. Nickel and Alumel™ were used as calibration standards.

Differential Scanning Calorimetry (DSC). DSC was performed using a TA Instruments 2920 differential scanning calorimeter. Temperature calibration was performed using NIST traceable indium metal. The sample was placed into an aluminum DSC pan, and the weight was accurately recorded. The pan was covered with a lid perforated with a laser pinhole, and the lid was crimped. A weighed, crimped aluminum pan was placed on the reference side of the cell. The sample cell was equilibrated at 25° C. and heated under a nitrogen purge at a rate of 10 K/min, up to a final temperature of 250° C. Differential Scanning Calorimetry data, like all thermal measurements, have variability associated with measurements. In DSC, such variability may be a result of pan configuration, heating rate, sample preparation, and colligative properties.

Single Crystal X-ray Diffraction (SCXRD). Datasets were collected on a Bruker SMART APEX II (cocrystals 1, 3 and 4) and Kappa APEX II (cocrystal 2) using MoKα radiation. Data were collected using APEXII software. APEXII v1.27, © 2005, Bruker Analytical X-ray Systems, Madison, Wis. Initial cell constants were found by small widely separated "matrix" runs. Data collection strategies were determined using COSMO. Scan speed and scan width were chosen based on scattering power and peak rocking curves. All datasets were collected at −153° C. using an Oxford Cryostream low-temperature device.

Unit cell constants and orientation matrices were improved by least-squares refinement of reflections thresholded from the entire dataset. Integration was performed with SAINT, (SAINT v6.02, © 1997-1999, Bruker Analytical X-ray Systems, Madison, Wis.) using this improved unit cell as a starting point. Precise unit cell constants were calculated in SAINT from the final merged dataset. Lorenz and polarization corrections were applied. Where indicated, absorption corrections were made using the multi-scan procedure in SADABS.

Data were reduced with SHELXTL (SHELXTL v5.10, © 1997, Bruker Analytical X-ray Systems, Madison, Wis.). The structures were solved in all cases by direct methods without incident. All hydrogens were assigned to idealized positions and were allowed to ride, except hydroxyl and urea protons.

Solid State $^{13}$C NMR Spectra. Solid state $^{13}$C NMR spectra were obtained using an Inova-400 spectrometer. The solid-state $^{13}$C cross polarization magic angle spinning (CP/MAS) NMR spectrum was acquired at ambient temperature on a Varian $^{UNITY}$INOVA-400 spectrometer (Larmor frequencies: $^{13}$C=100.542 MHz, $^{1}$H=399.799 MHz). The sample was packed into a 4 mm PENCIL type zirconia rotor and rotated at 12 kHz at the magic angle. The spectrum was acquired with phase modulated (TPPM) high power $^{1}$H decoupling during the acquisition time using a $^{1}$H pulse width of 2.9 μs (90°), a ramped amplitude cross polarization contact time of 4 ms, a 30 ms acquisition time, a 10 second delay between scans, a spectral width of 45 kHz with 2700 data points, and 100 co-added scans. The free induction decay (FID) was processed using Varian VNMR 6.1C software with 32768 points and an exponential line broadening factor of 10 Hz to improve the signal-to-noise ratio. The first three data points of the FID were back predicted using the VNMR linear prediction algorithm to produce a flat baseline. The chemical shifts of the spectral peaks were externally referenced to the carbonyl carbon resonance of glycine at 176.5 ppm.

Example 6

Characterization of 1:1 Pterostilbene:Caffeine Cocrystal, 1 (Form I)

Solids of cocrystal 1 (Form I) prepared by solvent-based conditions according to Example 1 were used for characterization except that single crystals were grown by vapor diffusion, as described.

6.1 XRPD Characterization. The XRPD pattern of cocrystal 1 (Form I), obtained using a PANalytical X'Pert Pro diffractometer, is shown in FIG. 2. Table 1 lists the peaks identified in the XRPD pattern of FIG. 2. Table 2 lists representative peaks from the XRPD pattern of FIG. 2. The representative peaks in Table 2, or a subset of those peaks, as well as the peaks in Table 1, or a subset of those peaks may be used to characterize cocrystal 1 (Form I).

TABLE 1

Cocrystal 1 (Form I).

| °2θ | d space (Å) | Intensity (%) |
|---|---|---|
| 6.94 ± 0.10 | 12.740 ± 0.186 | 6 |
| 9.45 ± 0.10 | 9.356 ± 0.100 | 92 |
| 10.08 ± 0.10 | 8.775 ± 0.088 | 92 |
| 11.97 ± 0.10 | 7.395 ± 0.062 | 30 |
| 12.53 ± 0.10 | 7.066 ± 0.057 | 8 |
| 12.91 ± 0.10 | 6.856 ± 0.053 | 8 |
| 13.77 ± 0.10 | 6.430 ± 0.047 | 53 |
| 13.92 ± 0.10 | 6.364 ± 0.046 | 22 |
| 14.64 ± 0.10 | 6.050 ± 0.041 | 3 |
| 15.16 ± 0.10 | 5.844 ± 0.039 | 28 |
| 16.02 ± 0.10 | 5.532 ± 0.035 | 12 |
| 16.43 ± 0.10 | 5.395 ± 0.033 | 8 |
| 16.81 ± 0.10 | 5.273 ± 0.031 | 37 |
| 17.10 ± 0.10 | 5.186 ± 0.030 | 17 |
| 17.89 ± 0.10 | 4.958 ± 0.028 | 3 |
| 18.72 ± 0.10 | 4.740 ± 0.025 | 13 |
| 18.99 ± 0.10 | 4.674 ± 0.025 | 13 |
| 19.24 ± 0.10 | 4.614 ± 0.024 | 27 |
| 19.94 ± 0.10 | 4.453 ± 0.022 | 11 |
| 20.25 ± 0.10 | 4.386 ± 0.022 | 3 |
| 20.51 ± 0.10 | 4.331 ± 0.021 | 3 |
| 20.73 ± 0.10 | 4.284 ± 0.021 | 4 |
| 21.28 ± 0.10 | 4.176 ± 0.019 | 8 |
| 21.84 ± 0.10 | 4.070 ± 0.018 | 24 |
| 22.43 ± 0.10 | 3.964 ± 0.018 | 5 |
| 23.24 ± 0.10 | 3.827 ± 0.016 | 8 |
| 23.54 ± 0.10 | 3.779 ± 0.016 | 5 |
| 23.95 ± 0.10 | 3.716 ± 0.015 | 7 |
| 24.39 ± 0.10 | 3.649 ± 0.015 | 6 |
| 24.70 ± 0.10 | 3.604 ± 0.014 | 6 |
| 25.20 ± 0.10 | 3.535 ± 0.014 | 8 |
| 25.97 ± 0.10 | 3.431 ± 0.013 | 100 |
| 26.42 ± 0.10 | 3.373 ± 0.013 | 74 |
| 26.90 ± 0.10 | 3.314 ± 0.012 | 10 |
| 27.16 ± 0.10 | 3.283 ± 0.012 | 6 |
| 27.70 ± 0.10 | 3.220 ± 0.011 | 5 |
| 27.92 ± 0.10 | 3.196 ± 0.011 | 8 |
| 28.33 ± 0.10 | 3.150 ± 0.011 | 11 |
| 28.59 ± 0.10 | 3.123 ± 0.011 | 6 |

TABLE 2

Cocrystal 1 (Form I).

| °2θ | d space (Å) | Intensity (%) |
|---|---|---|
| 9.45 ± 0.10 | 9.356 ± 0.100 | 92 |
| 10.08 ± 0.10 | 8.775 ± 0.088 | 92 |
| 13.77 ± 0.10 | 6.430 ± 0.047 | 53 |
| 25.97 ± 0.10 | 3.431 ± 0.013 | 100 |
| 26.42 ± 0.10 | 3.373 ± 0.013 | 74 |

6.2 TGA and DSC Characterization. FIG. 3 shows the TGA and DSC traces for cocrystal 1 (Form I). As shown in FIG. 3, the melting point of cocrystal 1 (Form I) is about 115° C. (114.33-115.59° C.). The traces may be used to characterize cocrystal 1 (Form I).

Figure 4:
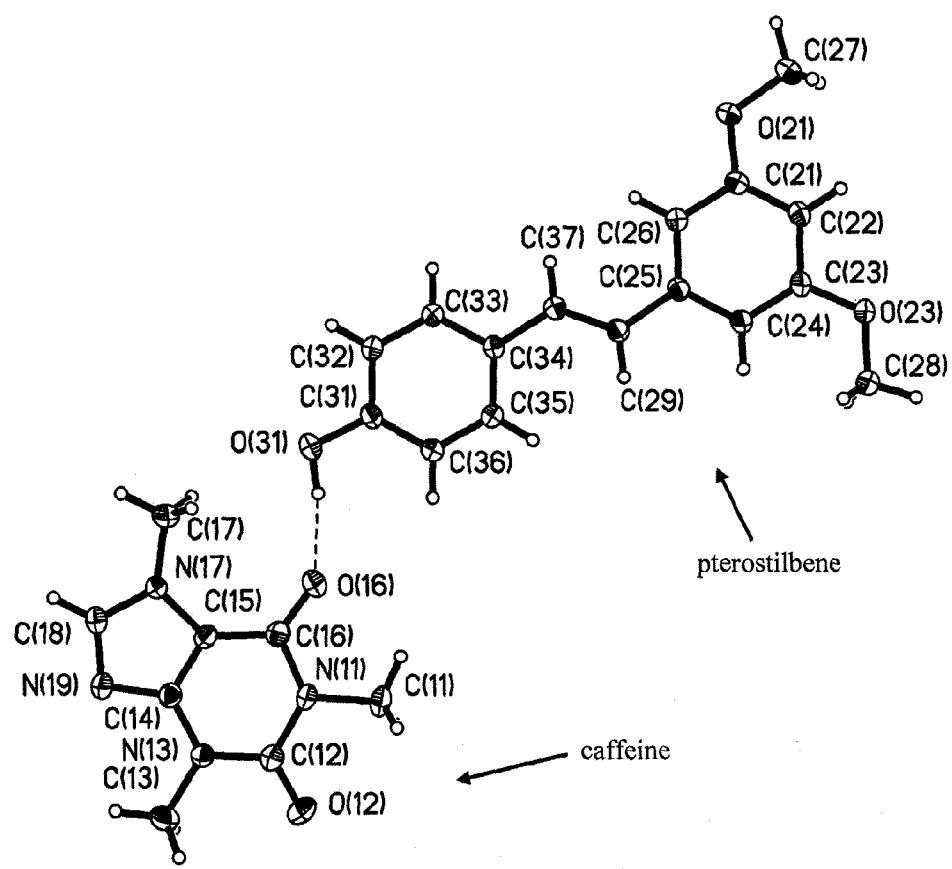
FIG. 4 shows an ORTEP drawing of the single-crystal X-ray structure of pterostilbene:caffeine cocrystal 1 (Form I).

6.3 Single Crystal Characterization. FIG. 4 shows an ORTEP drawing of cocrystal 1 (Form I). The complex crystallizes with two independent phenol/amine pairs per asymmetric unit. The two crystallographically nonequivalent pairs were distinguished with use of the SHELXL "RESI" command. Coordinates for the phenol protons H31 (on each pterostilbene) were allowed to refine. The crystal structure and data refinement parameters are reported in Table 3.

TABLE 3

Cocrystal 1 (Form I).

| | |
|---|---|
| Empirical formula | C24H26N4O5 |
| Formula weight | 450.49 |
| Temperature | 120(2) K |
| Wavelength | 0.71073 Å |
| Crystal system | Monoclinic |
| Space group | P2(1)/n |
| Unit cell dimensions | a = 17.4139(11) Å   α = 90° |
| | b = 13.3693(8) Å   β = 90.492(2)° |
| | c = 18.4844(10) Å   γ = 90° |
| Volume | 4303.2(4) Å$^3$ |
| Z | 8 |
| Density (calculated) | 1.391 g/cm$^3$ |
| Absorption coefficient | 0.099 mm$^{-1}$ |
| F(000) | 1904 |
| Crystal size | 0.32 × 0.18 × 0.10 mm$^3$ |
| Theta range for data collection | 1.60 to 33.14° |
| Index ranges | −25 <= h <= 17, −16 <= k <= 19, −27 <= l <= 28 |
| Reflections collected | 48373 |
| Independent reflections | 14776 [R(int) = 0.0428] |
| Completeness to theta = 30.00° | 99.2% |
| Absorption correction | None |
| Max. and min. transmission | 0.9902 and 0.9690 |
| Refinement method | Full-matrix least-squares on F$^2$ |
| Data/restraints/parameters | 14776/0/611 |
| Goodness-of-fit on F$^2$ | 1.064 |
| Final R indices [I > 2sigma(I)] | R1 = 0.0581, wR2 = 0.1606 |
| R indices (all data) | R1 = 0.0935, wR2 = 0.1833 |
| Largest diff. peak and hole | 0.620 and −0.309 e · Å$^{-3}$ |

In the crystal structure shown in FIG. 4, the two-component assemblies are held together through an O—H•O hydrogen bond from the hydroxyl moiety of pterostilbene to a carbonyl oxygen of caffeine. Hydrogen bond geometries for cocrystals 1 (Forms I and II) and cocrystal 2 are shown in Table 4 below.

TABLE 4

Hydrogen-Bond Geometries for 1 (Form I and II) and 2..

| Cocrystal | D-H•••A | d(H•••A)/Å | d(D•••A)/Å | θ(DHA)/deg |
|---|---|---|---|---|
| 1 (Form I) | O311-H311•••O161 | 1.80(3) | 2.7331(15) | 168.9(18) |
| | O312-H312•••O162 | 1.76(2) | 2.7112(15) | 169.0(17) |
| 1 (Form II) | O311-H311•••O161 | 1.80(3) | 2.716(3) | 175(3) |
| | O312-H312•••O162 | 1.96(3) | 2.725(2) | 169(3) |
| | O313-H313•••O163 | 1.68(3) | 2.719(2) | 174(3) |
| | O314-H314•••O164 | 1.91(3) | 2.716(3) | 175(3) |
| 2 | O41-H41•••O32 | 0.90(16) | 2.736(13) | 160(15) |
| | N31-H31A•••O32 | 0.88(17) | 2.872(15) | 174(15) |

Cocrystals of caffeine are not uncommon, with the Cambridge Structural Database (CSD v.5.31) listing 18 multi-component crystals where a carboxylic acid and/or hydroxyl moiety is present on the coformer and the crystallographic coordinates are determined. Not surprising, based on Etter's rules, when a carboxylic acid is present, the components are held together through O—H•N(caffeine) hydrogen bonds fifteen out of eighteen times, while if carboxylic acid and hydroxyl moeities are both present, O—H•O(caffeine) and/or O—H•N(caffeine) hydrogen bonds result the three remaining times. The hydrogen bonding pattern of cocrystal 1 was, therefore, unexpected since the O—N•N bond was not utilized, suggesting the energetics of the overall crystal packing are stronger than the hydrogen bonding interactions.

Figure 5A:
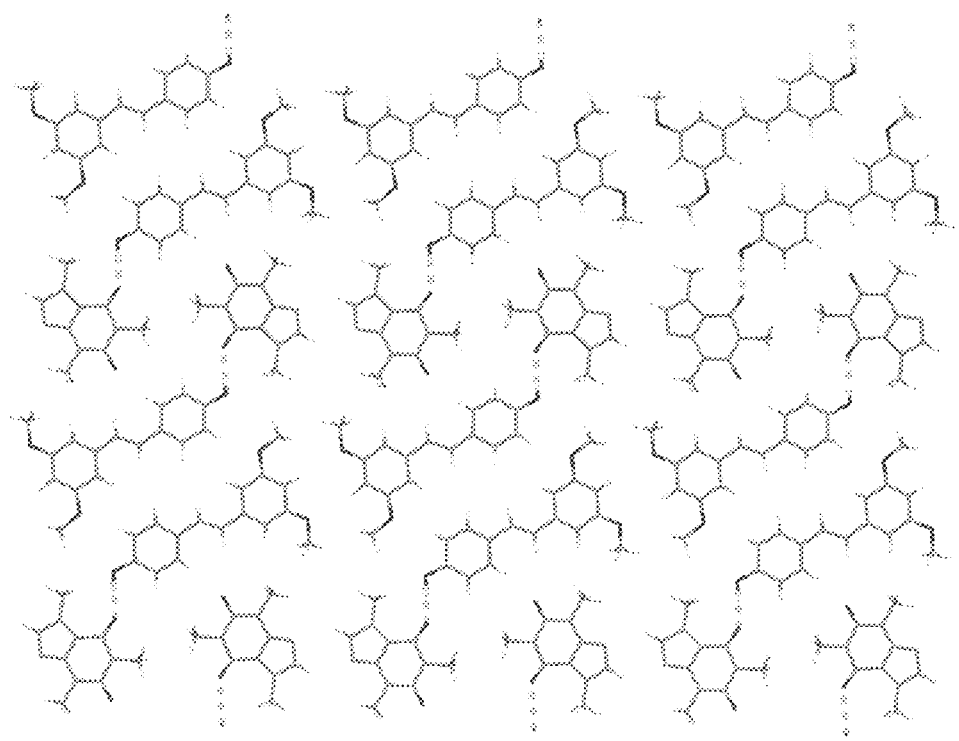
FIG. 5A shows a top-view of the two-dimensional sheet of cocrystal 1, displaying the rows of caffeine and pterostilbene.
Figure 5B:
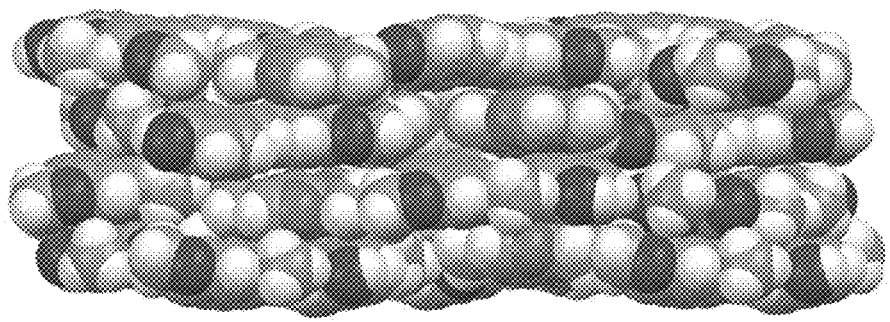
FIG. 5B shows a side-view of the relatively planar, stacked two-dimensional sheets of FIG. 5A.

The cocrystal assemblies pack in two-dimensional sheets through alternating rows of pterostilbene and caffeine molecules, while the stacked sheets result in a relatively planar arrangement in three-dimensions, as shown in FIGS. 5A and 5B, respectively.

Example 7

Characterization of 1:1 Pterostilbene:Caffeine Cocrystal, 1 (Form II)

Single crystals of cocrystal 1 (Form II) were grown by vapor diffusion, as reported in Example 2.

7.1 XRPD Characterization. The XRPD pattern of cocrystal 1 (Form II), obtained using a PANalytical X'Pert Pro diffractometer, is shown in FIG. 6. Table 5 lists the peaks identified in the XRPD pattern of FIG. 6. Table 6 lists representative peaks from the XRPD pattern of FIG. 6. The representative peaks in Table 6, or a subset of those peaks, as well as the peaks in Table 5, or a subset of those peaks may be used to characterize cocrystal 1 (Form II).

TABLE 5

| Cocrystal 1 (Form II). | | |
|---|---|---|
| °2θ | d space (Å) | Intensity (%) |
| 6.93 ± 0.10 | 12.755 ± 0.187 | 3 |
| 9.45 ± 0.10 | 9.355 ± 0.100 | 23 |
| 10.07 ± 0.10 | 8.782 ± 0.088 | 20 |
| 10.57 ± 0.10 | 8.367 ± 0.080 | 4 |
| 11.96 ± 0.10 | 7.400 ± 0.062 | 3 |
| 12.56 ± 0.10 | 7.047 ± 0.056 | 3 |
| 12.90 ± 0.10 | 6.865 ± 0.053 | 2 |
| 13.80 ± 0.10 | 6.418 ± 0.047 | 16 |
| 13.90 ± 0.10 | 6.372 ± 0.046 | 14 |
| 14.17 ± 0.10 | 6.252 ± 0.044 | 6 |
| 14.45 ± 0.10 | 6.130 ± 0.042 | 1 |
| 14.75 ± 0.10 | 6.005 ± 0.041 | 1 |
| 15.14 ± 0.10 | 5.854 ± 0.039 | 3 |
| 15.37 ± 0.10 | 5.765 ± 0.038 | 1 |
| 16.02 ± 0.10 | 5.532 ± 0.035 | 4 |
| 16.41 ± 0.10 | 5.403 ± 0.033 | 3 |
| 16.81 ± 0.10 | 5.275 ± 0.031 | 12 |
| 17.09 ± 0.10 | 5.188 ± 0.030 | 2 |
| 18.70 ± 0.10 | 4.746 ± 0.025 | 3 |
| 18.98 ± 0.10 | 4.676 ± 0.025 | 4 |
| 19.23 ± 0.10 | 4.616 ± 0.024 | 4 |
| 19.41 ± 0.10 | 4.572 ± 0.023 | 2 |
| 19.93 ± 0.10 | 4.455 ± 0.022 | 4 |
| 20.48 ± 0.10 | 4.336 ± 0.021 | 1 |
| 20.75 ± 0.10 | 4.281 ± 0.021 | 1 |
| 21.25 ± 0.10 | 4.181 ± 0.020 | 1 |
| 21.82 ± 0.10 | 4.073 ± 0.019 | 5 |
| 22.37 ± 0.10 | 3.974 ± 0.018 | 2 |
| 23.22 ± 0.10 | 3.830 ± 0.016 | 2 |
| 23.54 ± 0.10 | 3.779 ± 0.016 | 1 |
| 23.91 ± 0.10 | 3.722 ± 0.015 | 2 |
| 24.68 ± 0.10 | 3.608 ± 0.014 | 1 |
| 24.90 ± 0.10 | 3.577 ± 0.014 | 1 |
| 25.16 ± 0.10 | 3.539 ± 0.014 | 2 |
| 25.98 ± 0.10 | 3.430 ± 0.013 | 100 |
| 26.45 ± 0.10 | 3.370 ± 0.013 | 24 |

TABLE 5-continued

| Cocrystal 1 (Form II). | | |
|---|---|---|
| °2θ | d space (Å) | Intensity (%) |
| 26.90 ± 0.10 | 3.314 ± 0.012 | 3 |
| 27.15 ± 0.10 | 3.284 ± 0.012 | 2 |
| 28.32 ± 0.10 | 3.151 ± 0.011 | 4 |
| 29.54 ± 0.10 | 3.024 ± 0.010 | 2 |

TABLE 6

| Cocrystal 1 (Form II). | | |
|---|---|---|
| °2θ | d space (Å) | Intensity (%) |
| 9.45 ± 0.10 | 9.355 ± 0.100 | 23 |
| 10.07 ± 0.10 | 8.782 ± 0.088 | 20 |
| 25.98 ± 0.10 | 3.430 ± 0.013 | 100 |
| 26.45 ± 0.10 | 3.370 ± 0.013 | 24 |

7.2 TGA and DSC Characterization. FIG. 7 shows the TGA and DSC traces for cocrystal 1 (Form II). As shown in FIG. 7, the melting point of cocrystal 1 (Form II) is about 117° C. (115.81-118.07° C.). The traces may be used to characterize cocrystal 1 (Form II).

Figure 8:
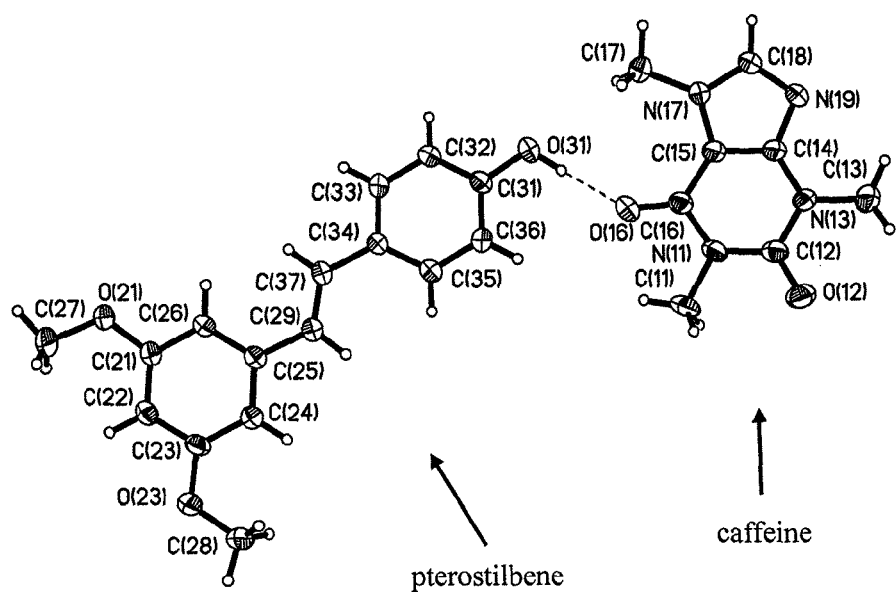
FIG. 8 shows an ORTEP drawing of the single-crystal X-ray structure of pterostilbene:caffeine cocrystal 1 (Form II).

7.3 Single Crystal Characterization. FIG. 8 shows an ORTEP drawing of cocrystal 1 (Form II). A small but significant degree of merohedral twinning (emulating orthorhombic) was handled using appropriate TWIN and BASF commands. The structure was divided into four chemically identical residues by using the SHELXL "RESI" command. Each residue contained one pterostilbene and one caffeine molecule. Coordinates for the four unique hydroxyl protons were allowed to refine. The crystal structure and data refinement parameters are reported in Table 7.

TABLE 7

| Cocrystal 1 (Form II). | |
|---|---|
| Empirical formula | C24H26N4O5 |
| Formula weight | 450.49 |
| Temperature | 120(2) K |
| Wavelength | 0.71073 Å |
| Crystal system | Monoclinic |
| Space group | P2(1)/n |
| Unit cell dimensions | a = 17.424(2) Å  α = 90° |
|  | b = 26.809(4) Å  β = 90.225(5)° |
|  | c = 18.546(2) Å  γ = 90° |
| Volume | 8663.1(18) Å$^3$ |
| Z | 16 |
| Density (calculated) | 1.382 g/cm$^3$ |
| Absorption coefficient | 0.098 mm$^{-1}$ |
| F(000) | 3808 |
| Crystal size | 0.25 × 0.20 × 0.15 mm$^3$ |
| Theta range for data collection | 0.76 to 32.03° |
| Index ranges | −22 <= h <= 25, −35 <= k <= 39, −22 <= l <= 27 |
| Reflections collected | 99700 |
| Independent reflections | 28191 [R(int) = 0.0655] |
| Completeness to theta = 27.50° | 99.3% |
| Absorption correction | None |
| Max. and min. transmission | 0.9854 and 0.9758 |
| Refinement method | Full-matrix least-squares on F$^2$ |
| Data/restraints/parameters | 28191/0/1222 |
| Goodness-of-fit on F$^2$ | 1.028 |
| Final R indices [I > 2sigma(I)] | R1 = 0.0728, wR2 = 0.1796 |
| R indices (all data) | R1 = 0.1316, wR2 = 0.2094 |
| Largest diff. peak and hole | 0.469 and −0.346 e · Å$^{-3}$ |

As can be seen from the discussion above, crystalline Form I and crystalline Form II of the pterostilbene:caffeine cocrystal 1 are not readily distinguishable by X-ray powder diffraction. Although polymorphs of compounds are typically distinguished by X-ray powder diffraction, occasionally, that task is challenging with conventional powder X-ray diffractometers. Here applicants have shown that there are two forms by single-crystal X-ray diffraction. The single crystal structures of Forms I and II are nearly identical in 5 of the 6 parameters which define a unit cell (three lengths and three angles) and crystallize with the same space group (P2(1)/n). One length, however, the "b" length differs in size between the two forms by a factor of two, making the unit cell volume of the smaller polymorph (Form I) one-half that of Form II. Single-crystal measurements similarly indicate that Form I has eight pterostilbene:caffeine molecular pairs per unit cell whereas Form II possesses sixteen.

Accordingly, by using X-ray powder diffraction, applicants can characterize a genus of pterostilbene:caffeine polymorphs, the genus including the species of Form I and Form II of the cocrystal 1. By using single-crystal X-ray powder analysis, applicants can distinguish and thus characterize either of Form I or Form II pterostilbene:caffeine. It may be possible to use other solid-state techniques to distinguish Form I from Form II of the pterostilbene:caffeine crystal 1.

Example 8

Characterization of Pterostilbene:Carbamazepine Cocrystal, 2

Solids of cocrystal 2 prepared by solvent-based conditions according to Example 3 were used for characterization except that single crystals were grown by vapor diffusion, as described.

Figure 9:
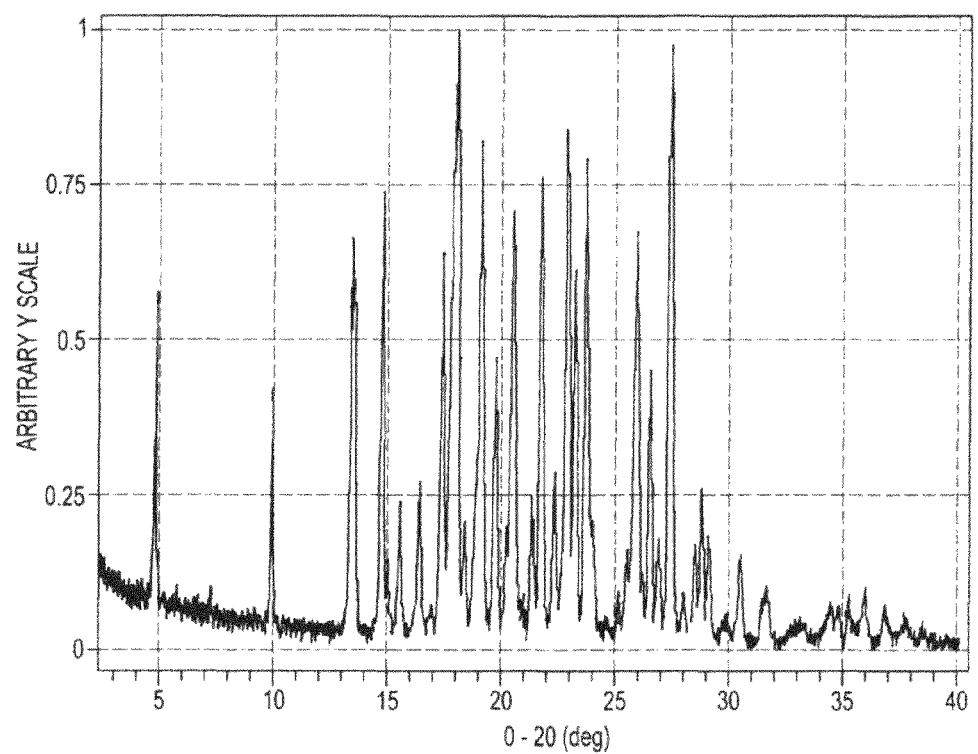
FIG. 9 shows the XRPD pattern of pterostilbene:carbamazepine cocrystal 2.

8.1 XRPD Characterization. The XRPD pattern of cocrystal 2, obtained using a PANalytical X'Pert Pro diffractometer, is shown in FIG. 9. Table 8 lists the peaks identified in the XRPD pattern of FIG. 9. Table 9 lists representative peaks from the XRPD pattern of FIG. 9. The representative peaks in Table 9, or a subset of those peaks, as well as the peaks in Table 8, or a subset of those peaks, may be used to characterize cocrystal 2.

TABLE 8

Cocrystal 2.

| °2θ | d space (Å) | Intensity (%) |
|---|---|---|
| 5.04 ± 0.10 | 17.528 ± 0.354 | 60 |
| 10.11 ± 0.10 | 8.754 ± 0.087 | 49 |
| 13.54 ± 0.10 | 6.540 ± 0.048 | 63 |
| 13.64 ± 0.10 | 6.492 ± 0.048 | 62 |
| 14.88 ± 0.10 | 5.955 ± 0.040 | 77 |
| 15.19 ± 0.10 | 5.832 ± 0.038 | 17 |
| 15.70 ± 0.10 | 5.643 ± 0.036 | 26 |
| 16.56 ± 0.10 | 5.352 ± 0.032 | 30 |
| 17.52 ± 0.10 | 5.061 ± 0.029 | 67 |
| 18.01 ± 0.10 | 4.926 ± 0.027 | 91 |
| 18.13 ± 0.10 | 4.892 ± 0.027 | 97 |
| 18.49 ± 0.10 | 4.798 ± 0.026 | 22 |
| 19.20 ± 0.10 | 4.624 ± 0.024 | 83 |
| 19.84 ± 0.10 | 4.475 ± 0.022 | 50 |
| 20.31 ± 0.10 | 4.373 ± 0.021 | 22 |
| 20.56 ± 0.10 | 4.320 ± 0.021 | 74 |
| 20.98 ± 0.10 | 4.234 ± 0.020 | 11 |
| 21.39 ± 0.10 | 4.155 ± 0.019 | 25 |
| 21.80 ± 0.10 | 4.076 ± 0.019 | 78 |
| 22.40 ± 0.10 | 3.970 ± 0.018 | 31 |
| 22.91 ± 0.10 | 3.883 ± 0.017 | 87 |
| 23.27 ± 0.10 | 3.822 ± 0.016 | 63 |
| 23.73 ± 0.10 | 3.749 ± 0.016 | 82 |

TABLE 8-continued

Cocrystal 2.

| °2θ | d space (Å) | Intensity (%) |
|---|---|---|
| 24.02 ± 0.10 | 3.705 ± 0.015 | 23 |
| 25.12 ± 0.10 | 3.545 ± 0.014 | 11 |
| 25.47 ± 0.10 | 3.497 ± 0.014 | 15 |
| 25.89 ± 0.10 | 3.442 ± 0.013 | 68 |
| 26.51 ± 0.10 | 3.363 ± 0.013 | 47 |
| 26.92 ± 0.10 | 3.312 ± 0.012 | 20 |
| 27.43 ± 0.10 | 3.252 ± 0.012 | 100 |
| 27.97 ± 0.10 | 3.190 ± 0.011 | 12 |
| 28.50 ± 0.10 | 3.132 ± 0.011 | 20 |
| 28.80 ± 0.10 | 3.100 ± 0.011 | 29 |
| 29.09 ± 0.10 | 3.070 ± 0.010 | 21 |

TABLE 9

Cocrystal 2.

| °2θ | d space (Å) | Intensity (%) |
|---|---|---|
| 5.04 ± 0.10 | 17.528 ± 0.354 | 60 |
| 10.11 ± 0.10 | 8.754 ± 0.087 | 49 |
| 13.54 ± 0.10 | 6.540 ± 0.048 | 63 |
| 13.64 ± 0.10 | 6.492 ± 0.048 | 62 |
| 14.88 ± 0.10 | 5.955 ± 0.040 | 77 |
| 17.52 ± 0.10 | 5.061 ± 0.029 | 67 |
| 18.01 ± 0.10 | 4.926 ± 0.027 | 91 |
| 18.13 ± 0.10 | 4.892 ± 0.027 | 97 |
| 19.20 ± 0.10 | 4.622 ± 0.024 | 85 |
| 19.84 ± 0.10 | 4.475 ± 0.022 | 50 |
| 20.56 ± 0.10 | 4.320 ± 0.021 | 74 |
| 21.80 ± 0.10 | 4.076 ± 0.019 | 78 |
| 22.91 ± 0.10 | 3.883 ± 0.017 | 87 |
| 23.27 ± 0.10 | 3.822 ± 0.016 | 63 |
| 23.73 ± 0.10 | 3.749 ± 0.016 | 82 |
| 25.89 ± 0.10 | 3.442 ± 0.013 | 68 |
| 27.43 ± 0.10 | 3.252 ± 0.012 | 100 |

Figure 10:
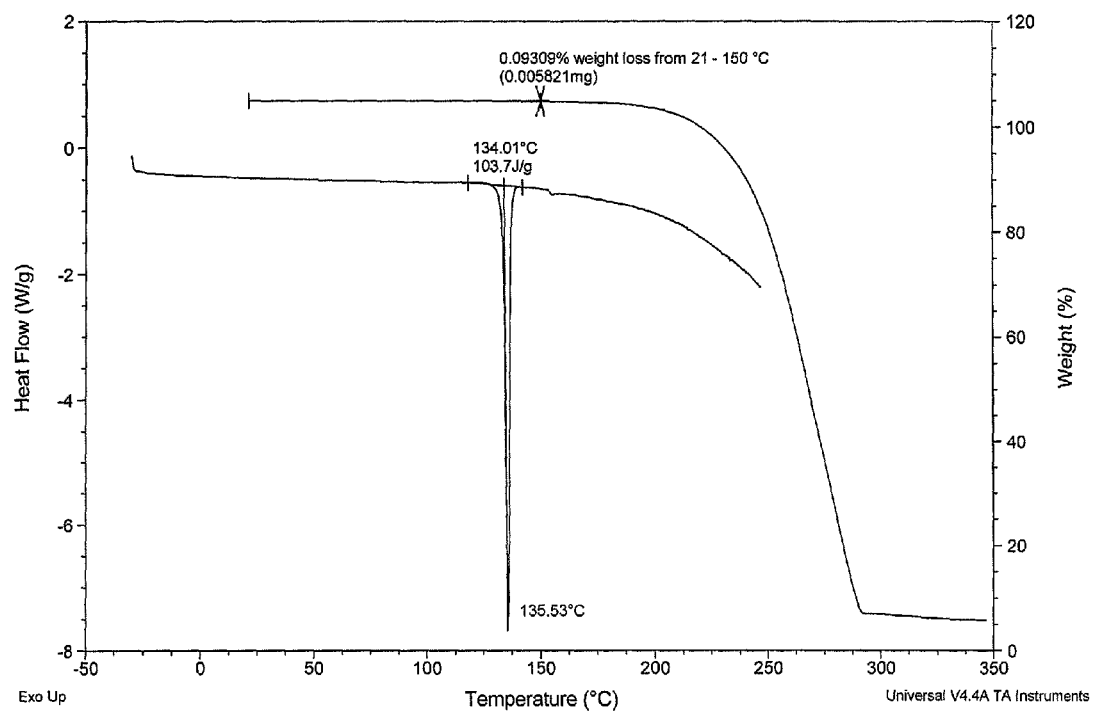
FIG. 10 shows the DSC and TGA traces of pterostilbene:carbamazepine cocrystal 2.

8.2 TGA and DSC Characterization. FIG. 10 shows the TGA and DSC traces for cocrystal 2. As shown in FIG. 10, the melting point of cocrystal 2 is about 135° C. (134.01-135.53° C.). The traces may be used to characterize cocrystal 2.

Figure 11:
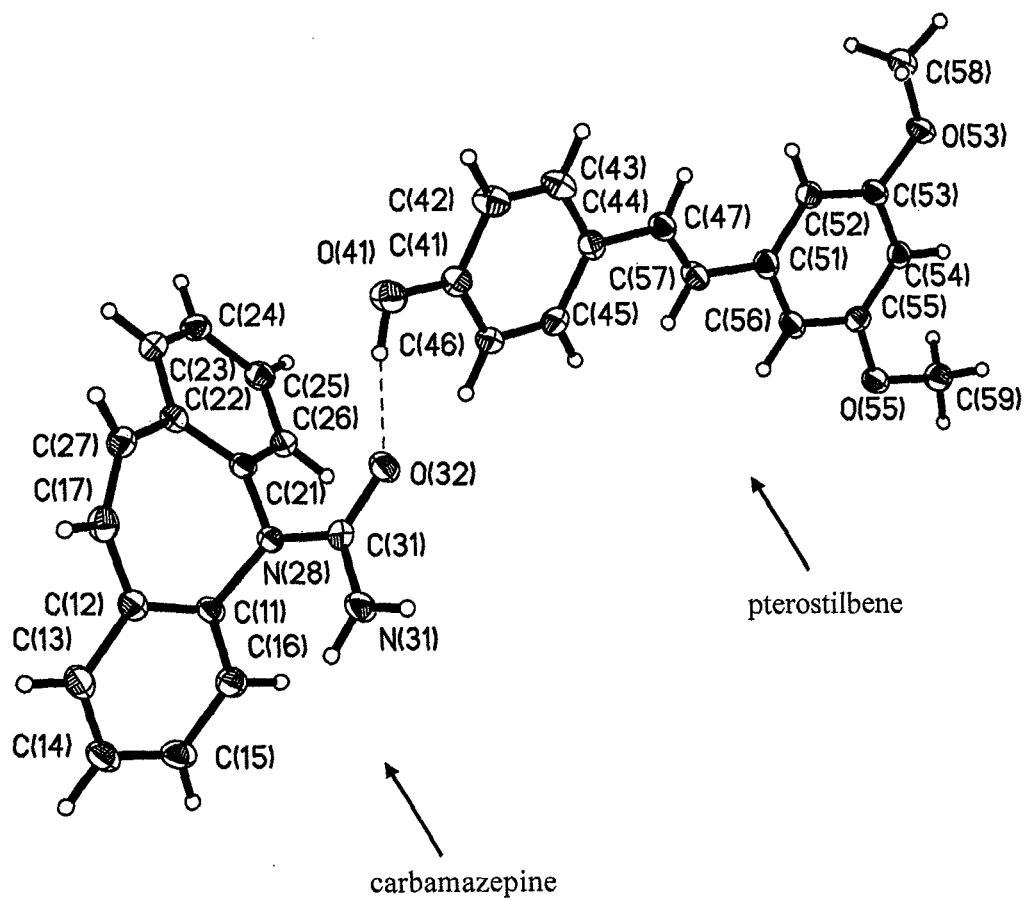
FIG. 11 shows an ORTEP drawing of the single-crystal X-ray structure of pterostilbene:carbamazepine cocrystal 2.

8.3 Single Crystal Characterization. FIG. 11 shows an ORTEP drawing of cocrystal 2. Coordinates for the urea protons and the hydroxyl proton were allowed to refine. The crystal structure and data refinement parameters are reported in Table 10. Cocrystal 2 crystallizes in a monclinic C2/c space group with Z=8. The asymmetric unit of cocrystal 2 contains pterostilbene and carbamazepine in a 1:1 stoichiometric ratio

TABLE 10

| Cocrystal 2. | | |
|---|---|---|
| Empirical formula | $C_{31}H_{28}N_2O_4$ | |
| Formula weight | 492.55 | |
| Temperature | 120(2) K | |
| Wavelength | 0.71073 Å | |
| Crystal system | Monoclinic | |
| Space group | C2/c | |
| Unit cell dimensions | a = 38.809(3) Å | α = 90° |
| | b = 5.3921(4) Å | β = 117.306(3)° |
| | c = 26.7284(17) Å | γ = 90° |
| Volume | 4969.9(6) Å$^3$ | |
| Z | 8 | |
| Density (calculated) | 1.317 g/cm$^3$ | |
| Absorption coefficient | 0.087 mm$^{-1}$ | |
| F(000) | 2080 | |
| Crystal size | 0.28 × 0.18 × 0.10 mm$^3$ | |
| Theta range for data collection | 1.57 to 32.54° | |

TABLE 10-continued

| Cocrystal 2. | |
|---|---|
| Index ranges | −56 <= h <= 56, −7 <= k <= 7, −39 <= l <= 40 |
| Reflections collected | 29297 |
| Independent reflections | 8372 [R(int) = 0.0616] |
| Completeness to theta = 30.00° | 99.2% |
| Absorption correction | None |
| Max. and min. transmission | 0.9913 and 0.9759 |
| Refinement method | Full-matrix least-squares on $F^2$ |
| Data/restraints/parameters | 8372/0/345 |
| Goodness-of-fit on $F^2$ | 1.085 |
| Final R indices [I > 2sigma(I)] | R1 = 0.0515, wR2 = 0.1208 |
| R indices (all data) | R1 = 0.0882, wR2 = 0.1361 |
| Largest diff. peak and hole | 0.386 and −0.256 e · Å$^{-3}$ |

Figure 12A:
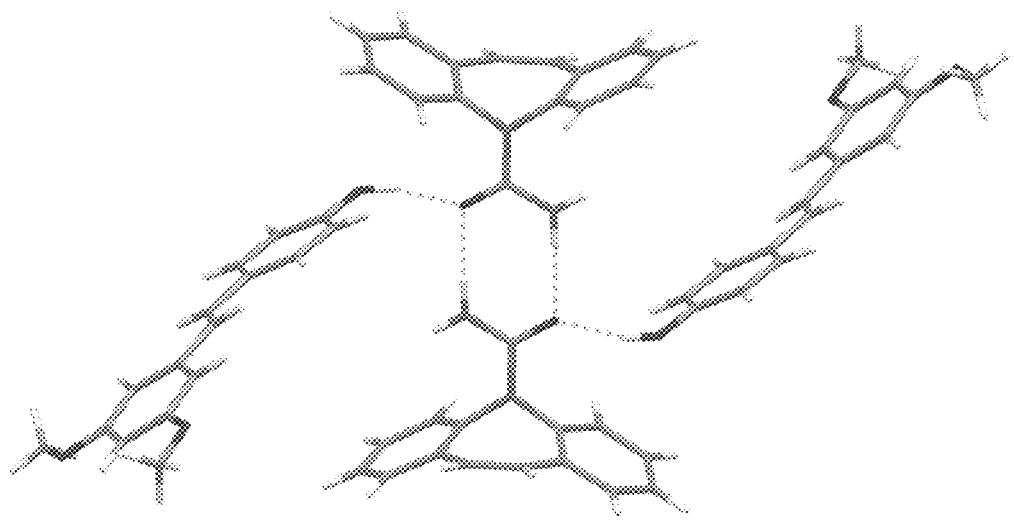
FIG. 12A shows a four-component supermolecule of cocrystal 2.
Figure 12B:
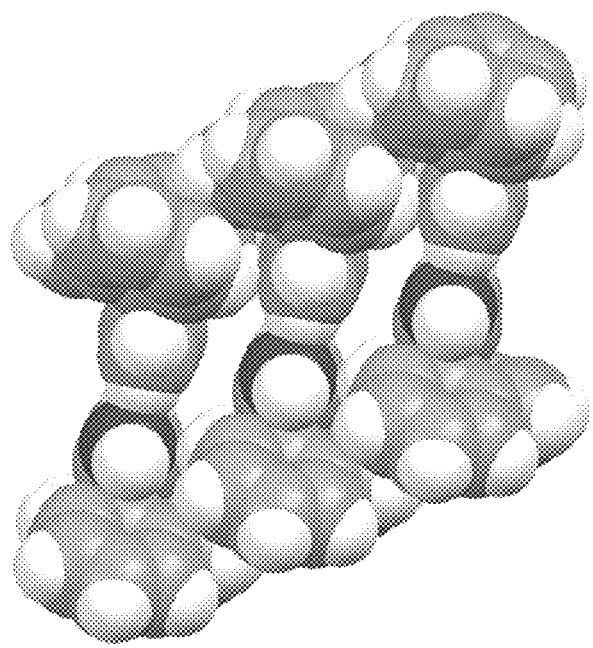
FIG. 12B shows a side-view of "translational stacked" carbamazepine dimers of cocrystal 2.

The components form a four-component supermolecule in which carbamazepine forms an amide:amide dimer through homomeric N—H•O hydrogen bonds, while the pterostilbene is linked through O—H•O hydrogen bonds from its hydroxyl group to the oxygen of the amide group on carbamazepine, as shown in FIG. 12A. The anti-amino proton of carbamazepine is not engaged in hydrogen bonding. In three-dimensions, the carbamazepine molecules pack in a "translation stack" motif, as shown in FIG. 12B, which is one of the more common packing motifs for multi-component crystals containing carbamazepine.

Example 9

Characterization of Pterostilbene:Glutaric Acid Cocrystal, 3

Solids of cocrystal 3 prepared by slow cooling according to Example 4 were used for characterization except that single crystals were grown by slow evaporation, as described.

Figure 13:
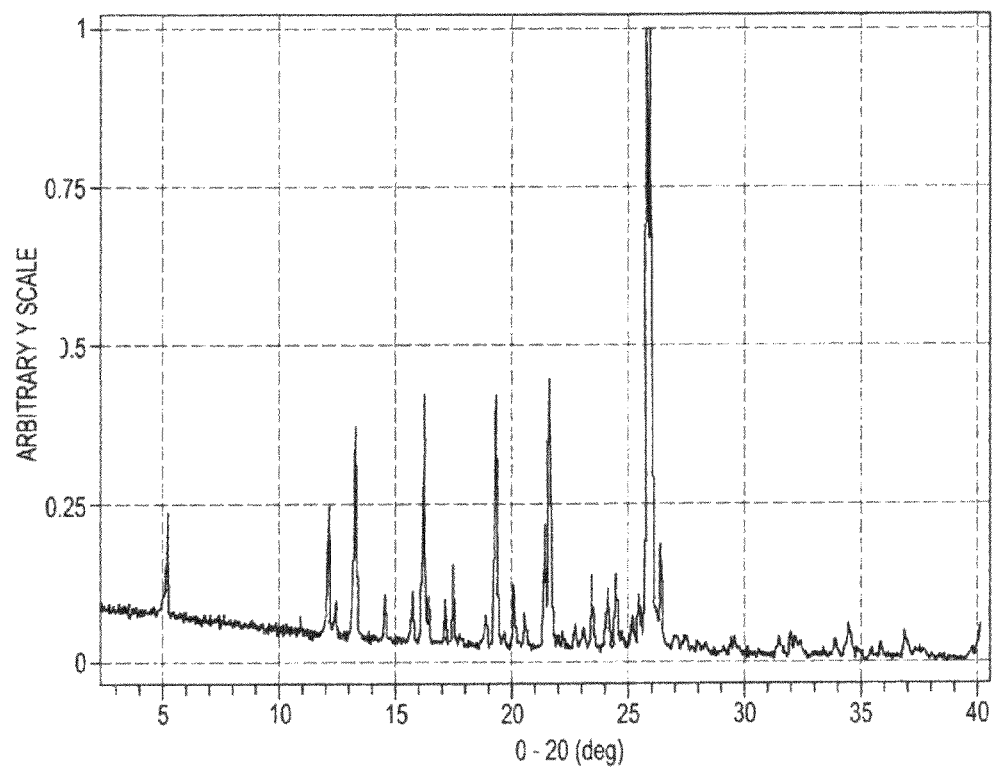
FIG. 13 shows the XRPD pattern of pterostilbene:glutaric acid cocrystal 3.

9.1 XRPD Characterization. The XRPD pattern of cocrystal 3, obtained using a PANalytical X'Pert Pro diffractometer, is shown in FIG. 13. Table 11 lists the peaks identified in the XRPD pattern of FIG. 13. Table 12 lists representative peaks from the XRPD pattern of FIG. 13. The representative peaks in Table 12, or a subset of those peaks, as well as the peaks in Table 11, or a subset of those peaks, may be used to characterize cocrystal 3.

TABLE 11

| Cocrystal 3. | | |
|---|---|---|
| °2θ | d space (Å) | Intensity (%) |
| 5.34 ± 0.10 | 16.560 ± 0.316 | 14 |
| 12.20 ± 0.10 | 7.252 ± 0.060 | 25 |
| 12.51 ± 0.10 | 7.078 ± 0.057 | 7 |
| 13.32 ± 0.10 | 6.645 ± 0.050 | 23 |
| 14.61 ± 0.10 | 6.063 ± 0.042 | 5 |
| 15.76 ± 0.10 | 5.622 ± 0.036 | 9 |
| 16.25 ± 0.10 | 5.455 ± 0.034 | 23 |
| 16.43 ± 0.10 | 5.394 ± 0.033 | 8 |
| 17.15 ± 0.10 | 5.170 ± 0.030 | 6 |
| 17.50 ± 0.10 | 5.067 ± 0.029 | 10 |
| 18.89 ± 0.10 | 4.698 ± 0.025 | 5 |
| 19.32 ± 0.10 | 4.593 ± 0.024 | 21 |
| 19.64 ± 0.10 | 4.520 ± 0.023 | 11 |
| 20.09 ± 0.10 | 4.419 ± 0.022 | 8 |
| 20.54 ± 0.10 | 4.323 ± 0.021 | 6 |
| 21.45 ± 0.10 | 4.143 ± 0.019 | 13 |
| 21.66 ± 0.10 | 4.102 ± 0.019 | 26 |
| 21.96 ± 0.10 | 4.047 ± 0.018 | 6 |
| 22.23 ± 0.10 | 3.999 ± 0.018 | 4 |
| 22.73 ± 0.10 | 3.912 ± 0.017 | 5 |
| 23.05 ± 0.10 | 3.859 ± 0.017 | 3 |
| 23.43 ± 0.10 | 3.796 ± 0.016 | 7 |
| 24.02 ± 0.10 | 3.705 ± 0.015 | 10 |
| 24.45 ± 0.10 | 3.640 ± 0.015 | 8 |
| 25.16 ± 0.10 | 3.540 ± 0.014 | 5 |
| 25.42 ± 0.10 | 3.504 ± 0.014 | 7 |
| 25.76 ± 0.10 | 3.459 ± 0.013 | 100 |
| 25.91 ± 0.10 | 3.439 ± 0.013 | 98 |
| 26.33 ± 0.10 | 3.385 ± 0.013 | 16 |
| 27.30 ± 0.10 | 3.267 ± 0.012 | 11 |
| 29.47 ± 0.10 | 3.031 ± 0.010 | 2 |

TABLE 12

| Cocrystal 3. | | |
|---|---|---|
| °2θ | d space (Å) | Intensity (%) |
| 12.20 ± 0.10 | 7.252 ± 0.060 | 25 |
| 13.32 ± 0.10 | 6.645 ± 0.050 | 23 |
| 16.25 ± 0.10 | 5.455 ± 0.034 | 23 |
| 19.32 ± 0.10 | 4.593 ± 0.024 | 21 |
| 21.66 ± 0.10 | 4.102 ± 0.019 | 26 |
| 25.76 ± 0.10 | 3.459 ± 0.013 | 100 |
| 25.91 ± 0.10 | 3.439 ± 0.013 | 98 |

Figure 14:
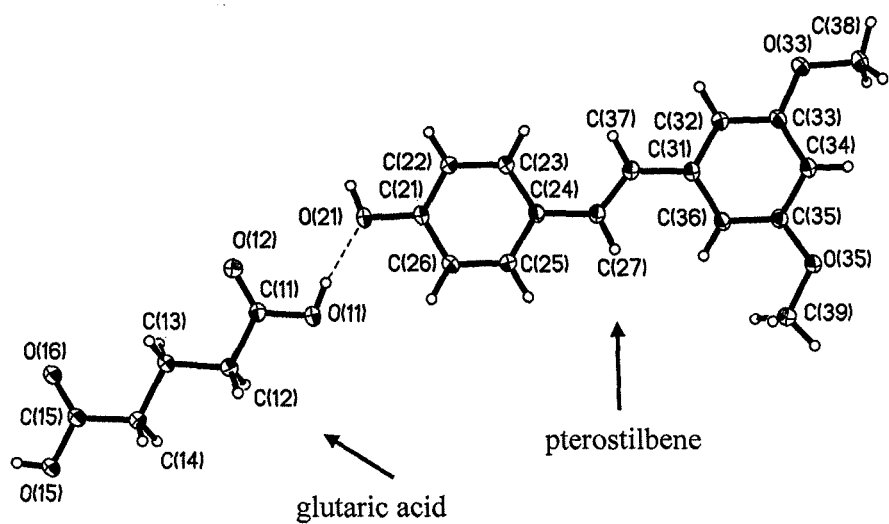
FIG. 14 shows an ORTEP drawing of the single-crystal X-ray structure of pterostilbene:glutaric acid cocrystal 3.

9.2 Single Crystal Characterization. FIG. 14 shows an ORTEP drawing of cocrystal 3. Coordinates for the carboxylic acid protons H11 and H15 and the phenol proton H21 were allowed to refine. The crystal structure and data refinement parameters are reported in Table 13.

TABLE 13

| Cocrystal 3. | |
|---|---|
| Empirical formula | C21H24O7 |
| Formula weight | 388.40 |
| Temperature | 120(2) K |
| Wavelength | 0.71073 Å |
| Crystal system | Monoclinic |
| Space group | P2(1)/c |
| Unit cell dimensions | a = 7.2644(3) Å  α = 90° |
| | b = 32.8801(16) Å  β = 96.000(2)° |
| | c = 7.9819(4) Å  γ = 90° |
| Volume | 1896.07(15) Å$^3$ |
| Z | 4 |
| Density (calculated) | 1.361 g/cm$^3$ |
| Absorption coefficient | 0.102 mm$^{-1}$ |
| F(000) | 824 |
| Crystal size | 0.26 × 0.14 × 0.08 mm$^3$ |
| Theta range for data collection | 1.24 to 32.58° |
| Index ranges | −11 <= h <= 6, −49 <= k <= 49, −11 <= l <= 12 |
| Reflections collected | 30177 |
| Independent reflections | 6677 [R(int) = 0.0280] |
| Completeness to theta = 32.58° | 96.9% |
| Absorption correction | None |
| Max. and min. transmission | 0.9919 and 0.9739 |
| Refinement method | Full-matrix least-squares on $F^2$ |
| Data/restraints/parameters | 6677/0/262 |
| Goodness-of-fit on $F^2$ | 1.086 |
| Final R indices [I > 2sigma(I)] | R1 = 0.0472, wR2 = 0.1224 |
| R indices (all data) | R1 = 0.0660, wR2 = 0.1396 |
| Largest diff. peak and hole | 0.570 and −0.254 e · Å$^{-3}$ |

Figure 15:
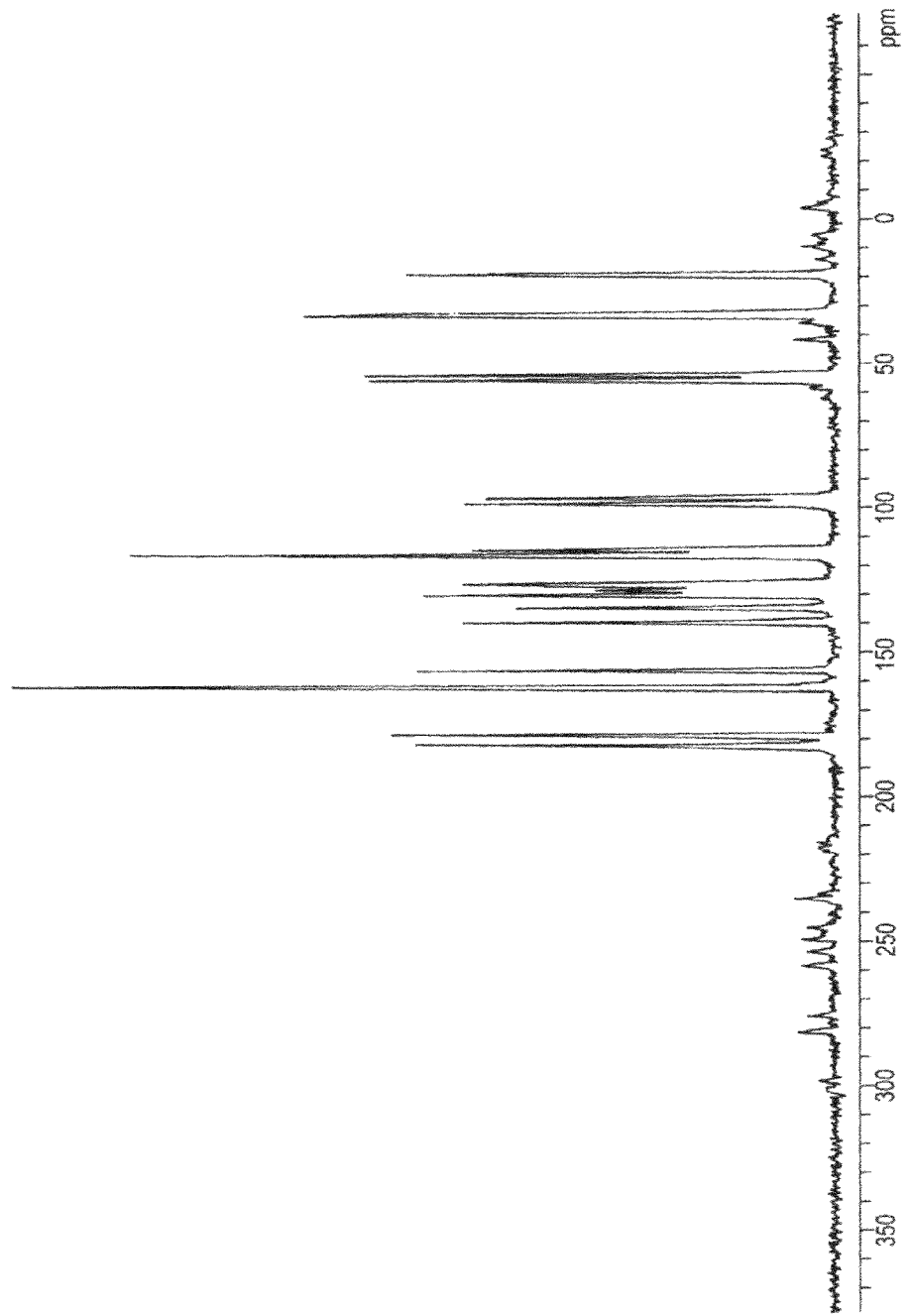
FIG. 15 shows the solid state $^{13}$C NMR spectrum of pterostilbene:glutaric acid cocrystal 3.
Figure 16:
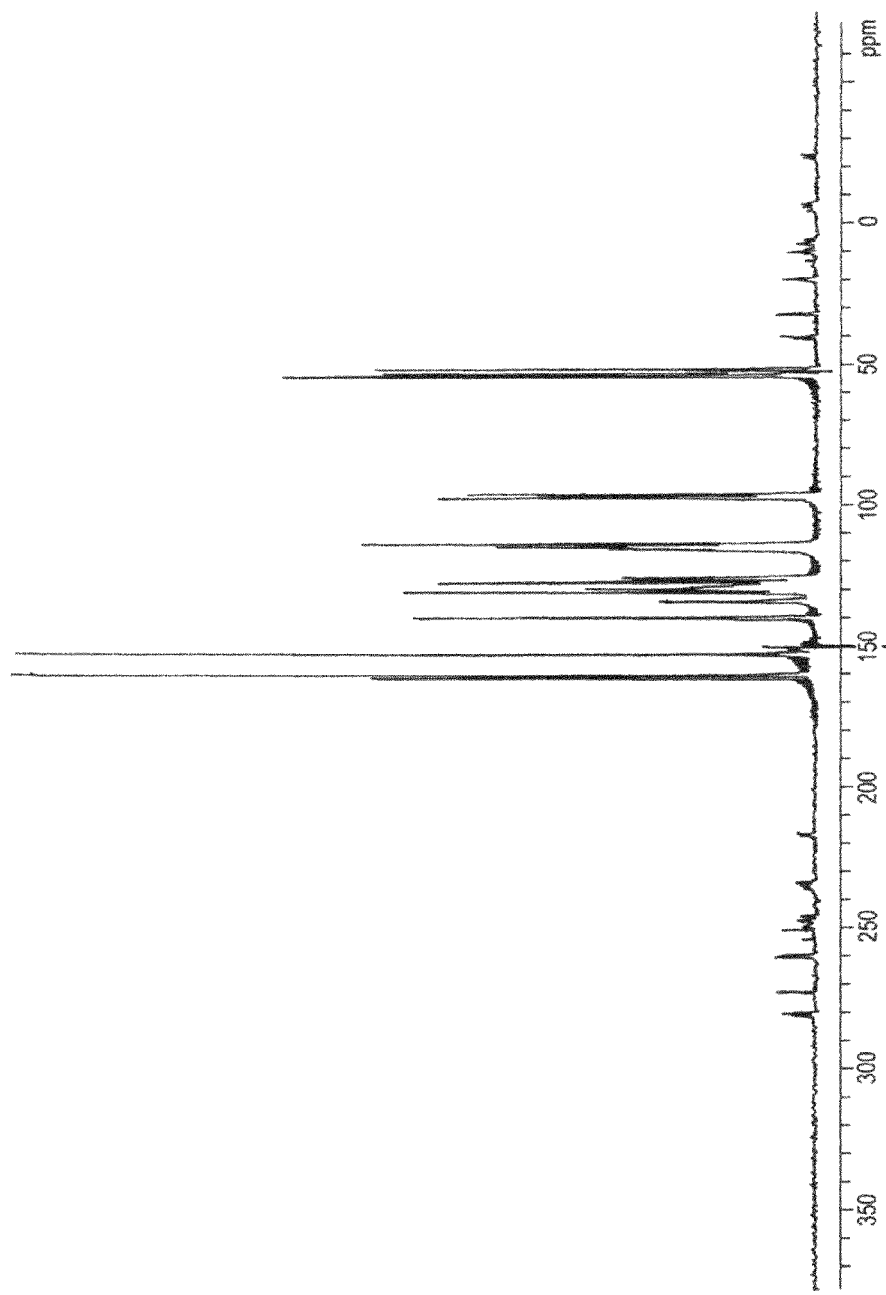
FIG. 16 shows the solid state $^{13}$C NMR spectrum of pterostilbene.
Figure 17:
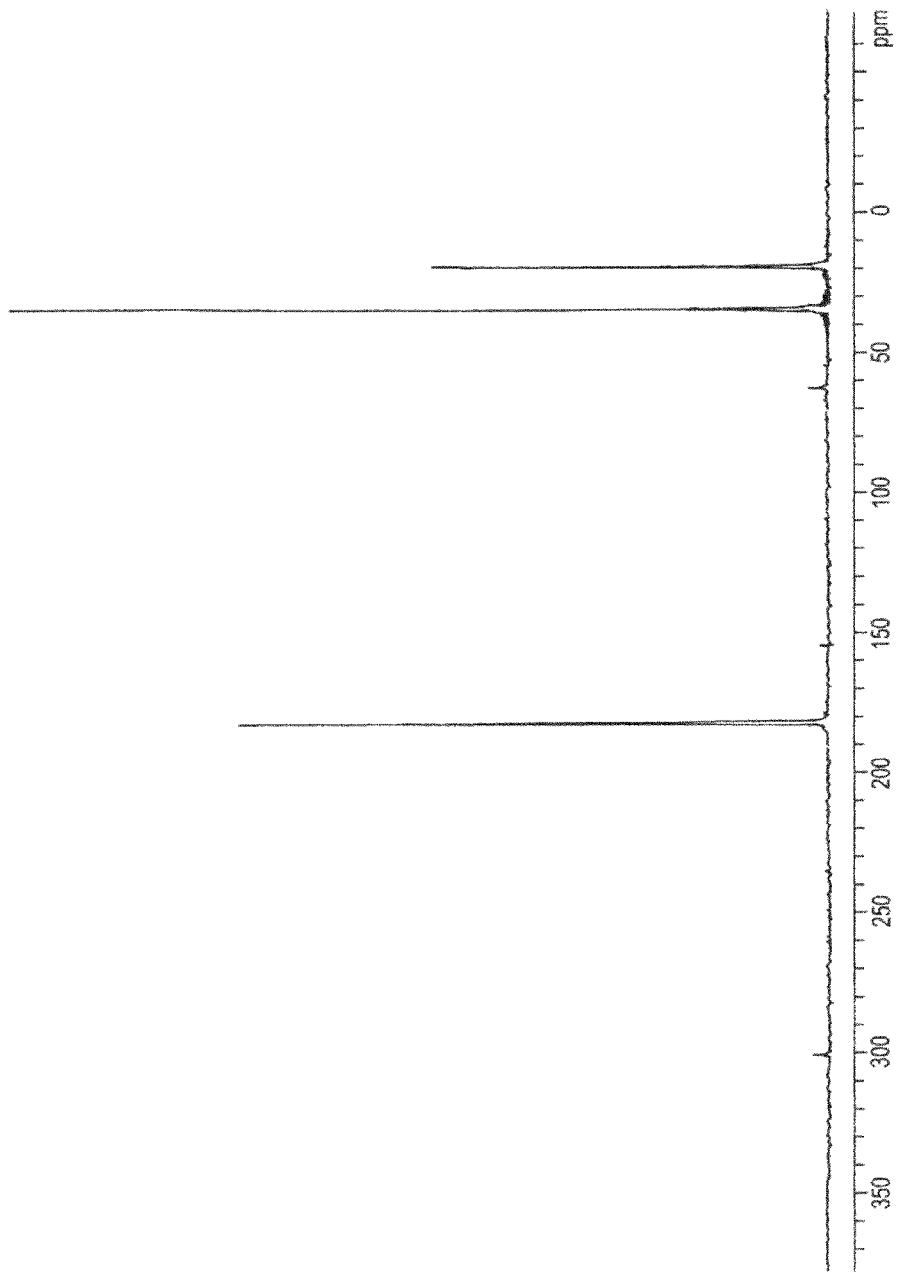
FIG. 17 shows the solid state $^{13}$C NMR spectrum of glutaric acid.

9.3 Solid State $^{13}$C NMR Characterization. FIG. 15 shows the solid state $^{13}$C NMR spectrum of cocrystal 3. The solid state $^{13}$C NMR spectra of pterostilbene and glutaric acid are shown in FIGS. 16 and 17, respectively. The spectrum may be used to characterize cocrystal 3.

Example 10

Characterization of Pterostilbene:Piperazine Cocrystal, 4

Solids of cocrystal 4 prepared by slow cooling according to Example 5 were used for characterization except that single crystals were grown by slow evaporation, as described.

Figure 18:
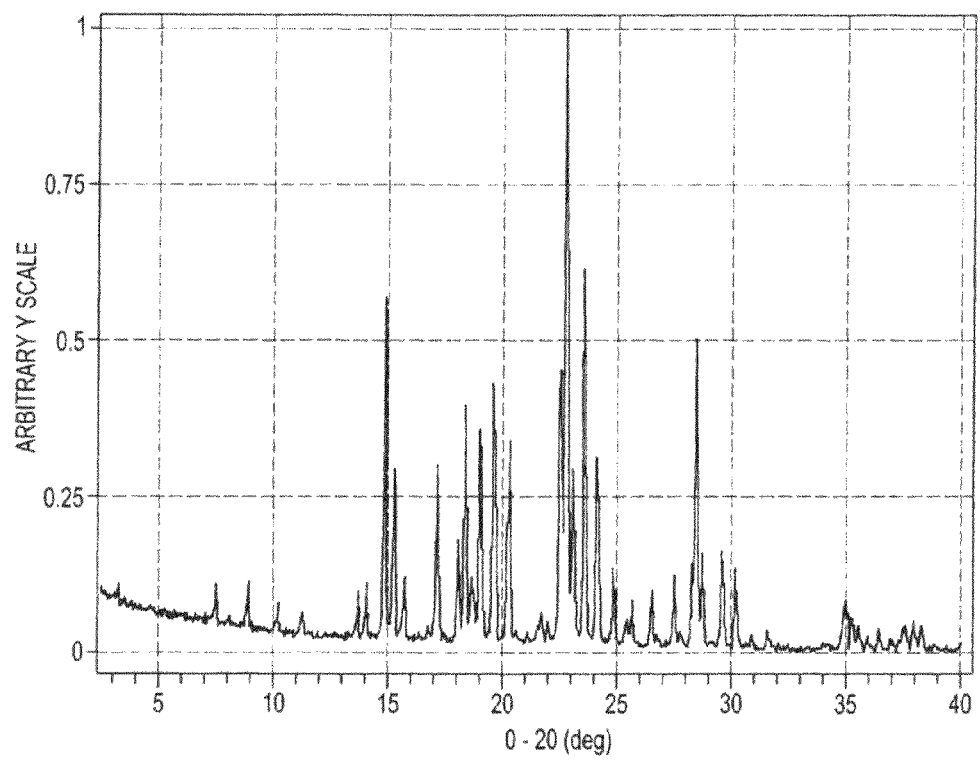
FIG. 18 shows the XRPD pattern of pterostilbene:piperazine cocrystal 4.

10.1 XRPD Characterization. The XRPD pattern of cocrystal 4, obtained using a PANalytical X'Pert Pro diffractometer, is shown in FIG. 18. Table 14 lists the peaks identified in the XRPD pattern of FIG. 18. Table 15 lists representative peaks from the XRPD pattern of FIG. 18. The representative peaks in Table 15, or a subset of those peaks, as well as the peaks in Table 14, or a subset of those peaks may be used to characterize cocrystal 4.

TABLE 14

| Cocrystal 4. | | |
|---|---|---|
| °2θ | d space (Å) | Intensity (%) |
| 3.42 ± 0.10 | 25.829 ± 0.778 | 12 |
| 7.63 ± 0.10 | 11.584 ± 0.154 | 12 |
| 9.05 ± 0.10 | 9.769 ± 0.109 | 12 |
| 10.29 ± 0.10 | 8.598 ± 0.084 | 9 |
| 11.38 ± 0.10 | 7.779 ± 0.069 | 8 |
| 13.75 ± 0.10 | 6.441 ± 0.047 | 10 |
| 14.15 ± 0.10 | 6.259 ± 0.044 | 12 |
| 14.93 ± 0.10 | 5.932 ± 0.040 | 57 |
| 15.34 ± 0.10 | 5.778 ± 0.038 | 30 |
| 15.80 ± 0.10 | 5.608 ± 0.035 | 12 |
| 16.86 ± 0.10 | 5.260 ± 0.031 | 6 |
| 17.26 ± 0.10 | 5.138 ± 0.030 | 31 |
| 18.11 ± 0.10 | 4.898 ± 0.027 | 19 |
| 18.43 ± 0.10 | 4.815 ± 0.026 | 40 |
| 18.68 ± 0.10 | 4.751 ± 0.025 | 13 |
| 19.08 ± 0.10 | 4.652 ± 0.024 | 36 |
| 19.61 ± 0.10 | 4.526 ± 0.023 | 44 |
| 20.33 ± 0.10 | 4.368 ± 0.021 | 34 |
| 21.10 ± 0.10 | 4.210 ± 0.020 | 4 |
| 21.74 ± 0.10 | 4.089 ± 0.019 | 7 |
| 21.99 ± 0.10 | 4.043 ± 0.018 | 6 |
| 22.57 ± 0.10 | 3.939 ± 0.017 | 46 |
| 22.77 ± 0.10 | 3.905 ± 0.017 | 100 |
| 23.11 ± 0.10 | 3.849 ± 0.017 | 29 |
| 23.56 ± 0.10 | 3.777 ± 0.016 | 62 |
| 24.13 ± 0.10 | 3.689 ± 0.015 | 32 |
| 24.81 ± 0.10 | 3.589 ± 0.014 | 15 |
| 25.40 ± 0.10 | 3.507 ± 0.014 | 6 |
| 25.60 ± 0.10 | 3.480 ± 0.013 | 9 |
| 26.47 ± 0.10 | 3.368 ± 0.013 | 11 |
| 26.73 ± 0.10 | 3.335 ± 0.012 | 4 |
| 27.42 ± 0.10 | 3.253 ± 0.012 | 13 |
| 27.75 ± 0.10 | 3.215 ± 0.011 | 4 |
| 28.24 ± 0.10 | 3.161 ± 0.011 | 15 |
| 28.39 ± 0.10 | 3.144 ± 0.011 | 51 |
| 28.65 ± 0.10 | 3.115 ± 0.011 | 17 |
| 29.51 ± 0.10 | 3.027 ± 0.010 | 17 |

TABLE 15

| Cocrystal 4. | | |
|---|---|---|
| °2θ | d space (Å) | Intensity (%) |
| 14.93 ± 0.10 | 5.932 ± 0.040 | 57 |
| 18.43 ± 0.10 | 4.815 ± 0.026 | 40 |
| 19.08 ± 0.10 | 4.652 ± 0.024 | 36 |
| 19.61 ± 0.10 | 4.526 ± 0.023 | 44 |
| 20.33 ± 0.10 | 4.368 ± 0.021 | 34 |
| 22.57 ± 0.10 | 3.939 ± 0.017 | 46 |
| 22.77 ± 0.10 | 3.905 ± 0.017 | 100 |
| 23.56 ± 0.10 | 3.777 ± 0.016 | 62 |
| 24.13 ± 0.10 | 3.689 ± 0.015 | 32 |
| 28.39 ± 0.10 | 3.144 ± 0.011 | 51 |

Figure 19:
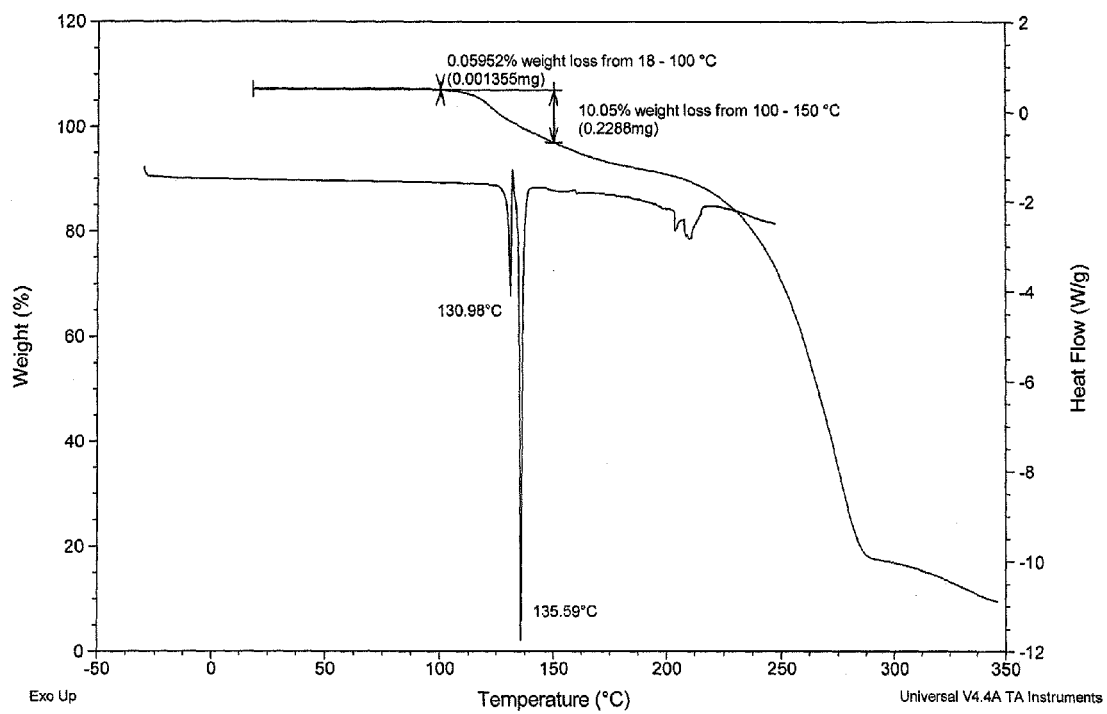
FIG. 19 shows the DSC and TGA traces of pterostilbene:piperazine cocrystal 4.

10.2 TGA and DSC Characterization. FIG. 19 shows the TGA and DSC traces for cocrystal 4. As shown in FIG. 19, the melting point of cocrystal 4 is about 133° C. (130.98-135.59° C.). The traces may be used to characterize cocrystal 4.

Figure 20:
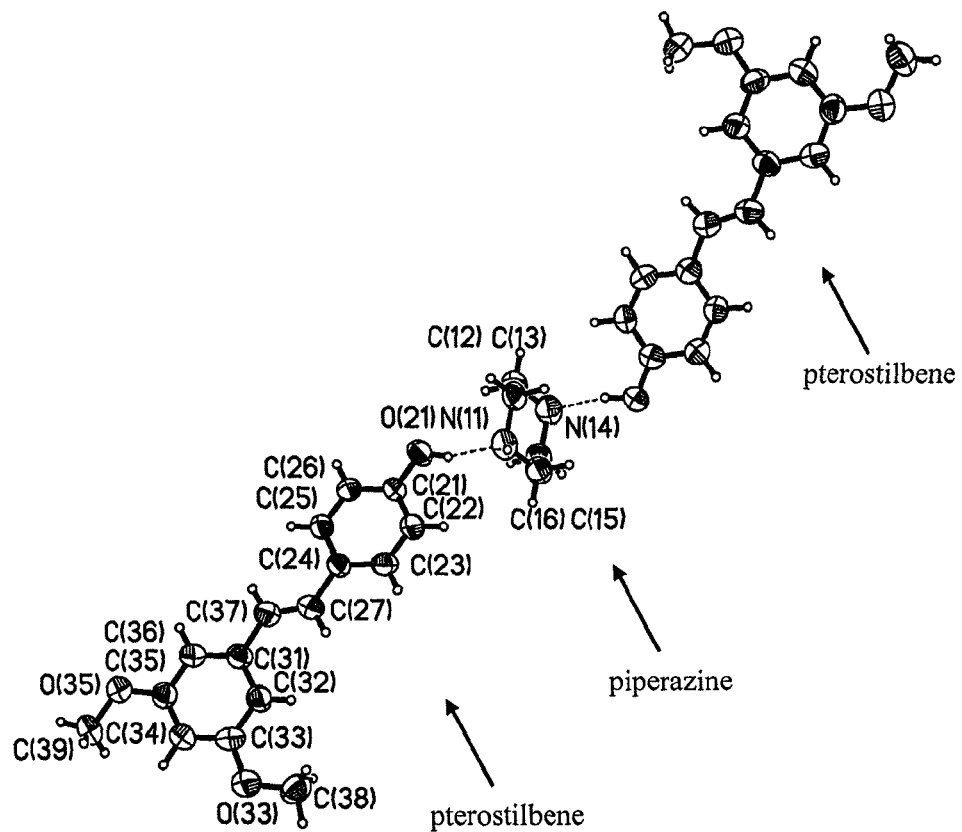
FIG. 20 shows an ORTEP drawing of the structure of pterostilbene:piperazine cocrystal 4.

10.3 Single Crystal Characterization. FIG. 20 shows an ORTEP drawing of cocrystal 4. The two crystallographically nonequivalent pterostilbenes were distinguished with use of the SHELXL "RESI" command. The compound crystallizes in the noncentrosymmetric space group $P2_12_12_1$. Due to the absence of heavy atom anomalous scatterers, determination of crystal handedness was not pursued, and Friedel oppposites were merged. Coordinates for the amine protons H11 & H14 and phenol protons H21 (on each pterostilbene) were allowed to refine. An extinction correction was applied; the EXTI parameter refined to a small but non-zero number. The crystal structure and data refinement parameters are reported in Table 16.

TABLE 16

| Cocrystal 4. | |
|---|---|
| Empirical formula | C36H42N2O6 |
| Formula weight | 598.72 |
| Temperature | 296(2) K |
| Wavelength | 0.71073 Å |
| Crystal system | Orthorhombic |
| Space group | P2(1)2(1)2(1) |
| Unit cell dimensions | a = 5.2586(7) Å    α = 90° |
|  | b = 11.7922(14) Å    β = 90° |
|  | c = 51.155(7) Å    γ = 90° |
| Volume | 3172.2(7) Å$^3$ |
| Z | 4 |
| Density (calculated) | 1.254 g/cm$^3$ |
| Absorption coefficient | 0.085 mm$^{-1}$ |
| F(000) | 1280 |
| Crystal size | 0.36 × 0.10 × 0.04 mm$^3$ |
| Theta range for data collection | 1.77 to 27.57° |
| Index ranges | −6 <= h <= 4, −15 <= k <= 11, −66 <= l <= 66 |
| Reflections collected | 37364 |
| Independent reflections | 4250 [R(int) = 0.0955] |
| Completeness to theta = 27.57° | 99.5% |
| Absorption correction | None |
| Max. and min. transmission | 0.9966 and 0.9700 |
| Refinement method | Full-matrix least-squares on F$^2$ |
| Data/restraints/parameters | 4250/0/414 |
| Goodness-of-fit on F$^2$ | 0.967 |
| Final R indices [I > 2sigma(I)] | R1 = 0.0545, wR2 = 0.0948 |
| R indices (all data) | R1 = 0.1713, wR2 = 0.1255 |
| Absolute structure parameter | 0(2) |
| Extinction coefficient | 0.0095(9) |
| Largest diff. peak and hole | 0.147 and −0.166 e · Å$^{-3}$ |

Example 11

Equilbrium Solubility of Pterostilbene:Carbamazepine Cocrystal 2 and Powder Dissolution of Pterostilbene:Caffeine Cocrystal 1 (Form I)

Solubility and concentration measurements were performed using ultraviolet (UV) spectroscopy on a Spectramax Microplate Reader. For carbamazepine and caffeine, standard curves were produced by serial dilutions; absorbance readings at 275 or 284 nm for caffeine or carbamazepine, respectively, were used to establish a linear regression. The small amount of methanol used to prepare carbamazepine standards did not cause shifting in the absorbance spectrum.

Figure 21:
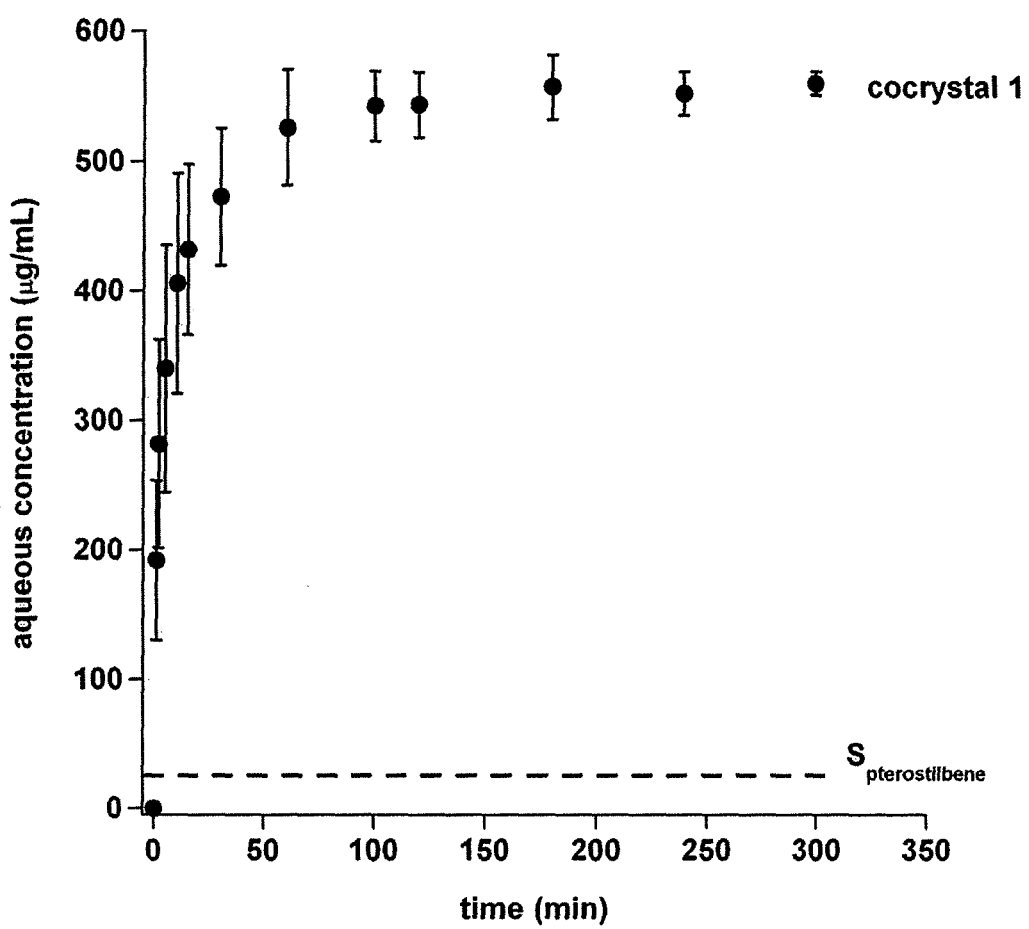
FIG. 21 shows a concentration vs. time profile for cocrystal 1 and equilibrium solubility of pterostilbene at ambient temperatures.
Figure 22:
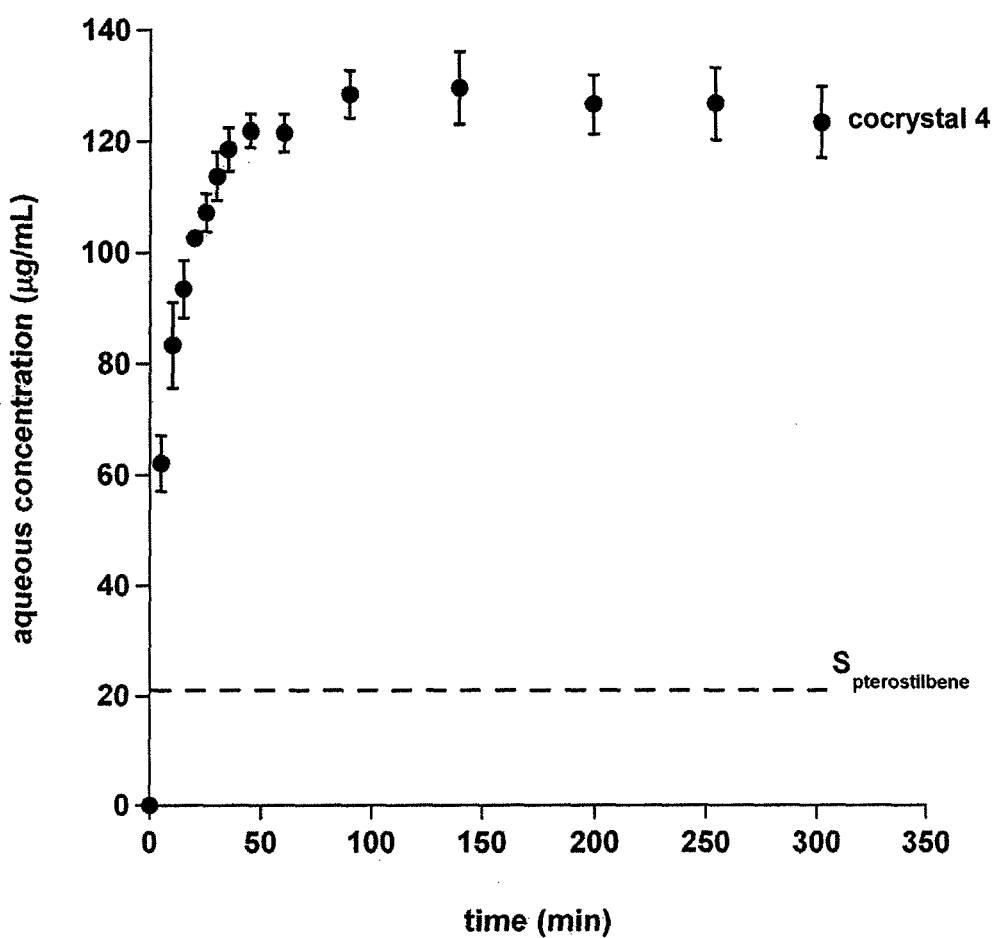
FIG. 22 shows a concentration vs. time profile for cocrystal 4 and equilibrium solubility of pterostilbene at ambient temperatures.

Caffeine, carbamazepine, and cocrystal 2 were slurried in water for 72 hours, filtered through a 0.2 μm nylon filter, and analyzed via a 96-well quartz plate in duplicate. Cocrystal 1 (Form I) was slurried in water, and aliquots were taken at specific time points to derive a concentration versus time profile to estimate the maximum concentration before transformation to pterostilbene occurred. Appropriate dilutions with water were made as necessary to maintain absorbance readings within the standard curve. All experiments were repeated three times to evaluate the standard deviation, while particle size was not controlled for any of the experiments. The equilibrium solubility measurement of pterostilbene Form I was determined by HPLC. The concentration at approximately 5 hours for cocrystal 1 (Form I) was 33 times lower compared to the solubility of caffeine hydrate, but was 27 times higher than pterostilbene's aqueous solubility. Cocrystal 2 showed a 7- and 2.5-fold decrease in solubility in comparison to carbamazepine and pterostilbene, respectively. The solubility measurements are reported in Table 17. FIG. 21 shows a concentration vs. time profile for cocrystal 1 (Form I) and equilibrium solubility of pterostilbene at ambient temperature.

TABLE 17

Solubility Data.

| Compounds | Solubility (± standard deviation) (μg/mL) |
|---|---|
| pterostilbene | 21[a] |
| caffeine | 18.5 (± 0.5) × 10³ |
| carbamazepine | 56 ± 4 |
| cocrystal 2 | 8.5 ± 0.7 |
| cocrystal 1 (Form I) | 560 ± 9[b] |

[a]Form I, PCT/US2010/22285
[b]concentration measurement at ~5 hours

Example 12

Relative Humidity Stability of Pterostilbene, Caffeine, Carbamazepine, Cocrystal 1 (Form I), and Cocrystal 2

The conversion between an anhydrate and hydrate (or vice versa) can be very problematic during the drug development process. One potential concern is a change in crystal form as a function of atmospheric humidity, which could lead to significantly different physicochemical properties between forms. Caffeine and carbamazepine are known to convert to a non-stoichiometric hydrate or dihydrate, respectively, at elevated humidity levels. Not suprising, the aqueous solubilities of the hydrate/anhydrate forms are considerably different. It has been previously shown that physical stability of APIs, known to convert to their respected hydrated forms, can be improved through cocrystal formation. Thus, cocrystals 1 and 2 are good candidates for a systematic study assessing the effects of increased RH in comparison to caffeine and carbamazepine.

Relative humidity (RH) conditions were created at ambient temperatures using saturated salt solutions: NaCl ~75%, $KNO_3$ ~94%, and $K_2SO_4$ ~98%. Vials of each sample containing approximately 10 mg, were subjected to physical stability at ~75% RH, ~94% RH, and ~98% RH for one day, three days, one week, and four weeks within a closed chamber. Pterostilbene was stressed at ~75% RH, ~94% RH, and ~98% RH for four weeks. Upon completion of the duration allowed, the samples were immediately analyzed by XRPD. The results are reported in Table 19.

TABLE 19

Stability Data.

| Stressed Material | Conditions, Time[a] | Results |
|---|---|---|
| pterostilbene (Form I) only | 75% RH, 4 weeks | pterostilbene (Form I) |
| | 94% RH, 4 weeks | pterostilbene (Form I) |
| | 98% RH, 4 weeks | pterostilbene (Form I) |
| caffeine only | 75% RH, 1 day | caffeine anhydrous |
| | 75% RH, 3 days | caffeine anhydrous |
| | 75% RH, 1 week | caffeine anhydrous |
| | 75% RH, 4 weeks | caffeine anhydrous |
| | 94% RH, 1 day | caffeine anhydrous |
| | 94% RH, 3 days | caffeine anhydrous/caffeine hydrate |
| | 94% RH, 1 week | caffeine hydrate |
| | 94% RH, 4 weeks | caffeine hydrate |
| | 98% RH, 1 day | caffeine hydrate |
| | 98% RH, 3 days | caffeine hydrate |
| | 98% RH, 1 week | caffeine hydrate |
| | 98% RH, 4 weeks | caffeine hydrate |
| cocrystal 1 (Form I) | 75% RH, 1 day | cocrystal 1 (Form I), no caffeine hydrate |
| | additional stress at 98% RH, 1 day | cocrystal 1 (Form I), no caffeine hydrate |
| | 75% RH, 3 days | cocrystal1 (Form I), no caffeine hydrate |
| | 75% RH, 1 week | cocrystal 1 (Form I), no caffeine hydrate |
| | additional stress at 98% RH, 1 week | cocrystal 1 (Form I), no caffeine hydrate |
| | 75% RH, 4 weeks | cocrystal 1 (Form I), no caffeine hydrate |
| | 94% RH, 1 day | cocrystal 1 (Form I), no caffeine hydrate |
| | additional stress at 98% RH, 3 days | — |
| | 94% RH, 3 days | cocrystal 1 (Form I), no caffeine hydrate |
| | 94% RH, 7 days | cocrystal 1 (Form I), no caffeine hydrate |
| | additional stress at 98% RH, 4 weeks | cocrystal 1 (Form I), no caffeine hydrate |
| | 94% RH, 4 weeks | cocrystal 1 (Form I), no caffeine hydrate |
| | slurry, 2 days | cocrystal 1 (Form I), no caffeine hydrate |

TABLE 19-continued

Stability Data.

| Stressed Material | Conditions, Time[a] | Results |
|---|---|---|
| carbamazepine only | 75% RH, 1 day | carbamazepine (Form III) |
| | 75% RH, 3 days | carbamazepine (Form III) |
| | 75% RH, 1 week | carbamazepine (Form III) |
| | 75% RH, 4 weeks | carbamazepine (Form III) |
| | 94% RH, 1 day | carbamazepine (Form III) |
| | 94% RH, 3 days | carbamazepine (Form III) |
| | 94% RH, 1 week | carbamazepine (Form III) + small amount of dihydrate |
| | 94% RH, 4 weeks | carbamazepine dihydrate + small amount of carbamazepine (Form III) |
| | 98% RH, 1 day | carbamazepine (Form III) + small amount of dihydrate |
| | 98% RH, 3 days | carbamazepine (Form III) + small amount of dihydrate |
| | 98% RH, 1 week | carbamazepine dihydrate + small amount of carbamazepine (Form III) |
| | 98% RH, 4 weeks | carbamazepine dihydrate |
| cocrystal 2 | 75% RH, 1 day | cocrystal 2, no carbamazepine dihydrate |
| | 75% RH, 3 days | cocrystal 2, no carbamazepine dihydrate |
| | 75% RH, 1 week | cocrystal 2, no carbamazepine dihydrate |
| | 75% RH, 4 weeks | cocrystal 2, no carbamazepine dihydrate |
| | 94% RH, 1 day | cocrystal 2, no carbamazepine dihydrate |
| | 94% RH, 3 days | cocrystal 2, no carbamazepine dihydrate |
| | 94% RH, 1 week | cocrystal 2, no carbamazepine dihydrate |
| | 94% RH, 4 weeks | cocrystal 2, no carbamazepine dihydrate |
| | 98% RH, 1 day | cocrystal 2, no carbamazepine dihydrate |
| | 98% RH, 3 days | cocrystal 2, no carbamazepine dihydrate |
| | 98% RH, 1 week | cocrystal 2, no carbamazepine dihydrate |
| | 98% RH, 4 weeks | cocrystal 2, no carbamazepine dihydrate |

[a]All % RH conditions and stressing times are approximate.

As noted above, caffeine does not display signs of conversion at 75% RH up to four weeks; however, between one and three days at 94% RH partial conversion is observed, while at 98% RH anhydrous caffeine converts to caffeine hydrate in less than one day. In comparison, cocrystal 1 showed remarkable physical stability displaying no dissociation at 75, 94, or 98% RH after four weeks by XRPD. Carbamazepine shows similar hydration patterns to caffeine, in that no conversion is observed at 75% RH, while at 94% RH anhydrous carbamazepine partially converts to the dihydrate between three days and one week. Full conversion to the dihydrate is observed in less than one day at 98% RH. Once again, pterostilbene improves the physical stability of caffeine, as observed by no dissociation of cocrystal 3 into its individual components at 75, 94, or 98% RH after four weeks.

Example 13

Physical Stability of Pterostilbene:Glutaric Acid Cocrystal 3 and Pterostilbene:Piperazine Cocrystal 4

Physical stability was evaluated at approximately 40° C., 60° C., 25° C./75% RH, 25° C./98% RH, and 40° C./75% RH and XRPD was used to detect dissociation or form conversion. Vials of each cocrystal were subjected to each condition for durations of two weeks, one month, and two months. Upon completion of the duration allowed, the samples were immediately analyzed by XRPD. The results are reported in Table 20.

TABLE 20

Stability Data.

| Stressed Material | Conditions, Time[a] | Results (by XRPD) |
|---|---|---|
| cocrystal 3 | 40° C., 2 weeks | cocrystal 3 |
| | 40° C., 4 weeks | cocrystal 3 |
| | 40° C., 8 weeks | cocrystal 3 |
| | 60° C., 2 weeks | cocrystal 3 |
| | 60° C., 4 weeks | cocrystal 3 |
| | 60° C., 8 weeks | cocrystal 3 |
| | 25° C./75% RH, 2 weeks | cocrystal 3 |
| | 25° C./75% RH, 4 weeks | cocrystal 3 |
| | 25° C./75% RH, 8 weeks | cocrystal 3 |
| | 25° C./98% RH, 2 weeks | cocrystal 3 |
| | 25° C./98% RH, 4 weeks | cocrystal 3 |
| | 25° C./98% RH, 8 weeks | cocrystal 3 |
| | 40° C./75% RH, 2 weeks | cocrystal 3 |
| | 40° C./75% RH, 4 weeks | cocrystal 3 |
| | 40° C./75% RH, 8 weeks | cocrystal 3 |
| cocrystal 4 | 40° C., 2 weeks | cocrystal 4 |
| | 40° C., 4 weeks | cocrystal 4 |
| | 40° C., 8 weeks | cocrystal 4 |
| | 60° C., 2 weeks | cocrystal 4 |
| | 60° C., 4 weeks | cocrystal 4 |
| | 60° C., 8 weeks | cocrystal 4 |
| | 25° C./75% RH, 2 weeks | cocrystal 4 |
| | 25° C./75% RH, 4 weeks | cocrystal 4 |
| | 25° C./75% RH, 8 weeks | cocrystal 4 |
| | 25° C./98% RH, 2 weeks | cocrystal 4 |
| | 25° C./98% RH, 4 weeks | cocrystal 4 |
| | 25° C./98% RH, 8 weeks | cocrystal 4 |
| | 40° C./75% RH, 2 weeks | cocrystal 4 |
| | 40° C./75% RH, 4 weeks | cocrystal 4 |
| | 40° C./75% RH, 8 weeks | cocrystal 4 |

[a]All % RH conditions and stressing times are approximate.

Example 14

Powder Dissolution of Pterostilbene:Piperazine Cocrystal 4 and attempted Pterostilbene:Glutaric Acid Cocrystal 3

Concentration measurements were performed using ultraviolet (UV) spectroscopy on a Spectramax Microplate Reader. For pterostilbene, a standard curve was produced by serial dilutions; absorbance readings at 315 nm for pterostilbene were used to establish a linear regression. The small amount of methanol used to prepare pterostilbene standards did not cause shifting in the absorbance spectrum.

Cocrystal 4 was slurried in water at ambient, and aliquots were taken at specific time points to derive a concentration versus time profile to estimate the maximum concentration before transformation to pterostilbene occurred. Aliquots were centrifuged; supernatant was extracted, and appropriate dilutions were made to maintain absorbance readings within the standard curve. Absorbance measurements were taken at 315 nm for pterostilbene, and concentrations were calculated from the standard curve. All experiments were repeated three times to evaluate the standard deviation, while particle size was not controlled for any of the experiments. The concentration measurement at approximately five hours for cocrystal 4 is reported in Table 21.

TABLE 21

Solubility Data.

| Compounds | Solubility (±standard deviation) μg/mL |
|---|---|
| pterostilbene | 21[a] |
| cocrystal 4 | 123 ± 6[b] |

[a]Form I, PCT/US/2010/22285
[b]concentration measurement at ~5 hours

Attempted Powder and Intrinsic Dissolution of Pterostilbene:Glutaric Acid Cocrystal.

Powder dissolution of cocrystal 3 was attempted under the same experimental conditions as the cocrystal 4. However, XRPD results indicate crystalline pterostilbene after 5 minutes when slurrying in water at ambient. Intrinsic dissolution in 900 mL water at ambient conditions was also attempted. However, XRPD results indicate crystalline pterostilbene after 30 minutes. Therefore, a concentration vs. time and intrinsic dissolution rate value were unobtainable at these conditions. However, due to crystalline pterostilbene being the only product observed by XRPD after slurrying in water, we can conclude the solubility of cocrystal 3 is greater than the solubility of pterostilbene.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. For example, the invention contemplates the possibility of the presence of at least some hydrated or solvated cocrystals, free API or free coformers in the crystalline structures. Accordingly, it is intended that the invention be limited only to the extent required by the appended claims and the applicable rules of law.

We claim:

1. A pterostilbene:carbamazepine cocrystal.
2. The cocrystal according to claim 1, wherein the molar ratio of pterostilbene:carbamazepine is 1:1.
3. The cocrystal according to claim 1 having unique peaks at about 5.04, 10.11, 13.54, 13.64, 14.88, 17.52, 18.01, 18.13, 19.20, 19.84, 20.56, 21.80, 22.91, 23.27, 23.73, 25.89 degrees two theta (±0.10 degrees) when analyzed by powder X-ray diffraction using Cu K-alpha radiation.
4. The cocrystal according to claim 1 having the powder X-ray diffraction pattern shown in FIG. 9.
5. A pterostilbene:carbamazepine cocrystal having a solid phase melting point at about 135° C. measured by DSC.
6. A solid composition comprising:
   an amount of pterostilbene:carbamazepine cocrystals; and
   one or more excipients.
7. The composition according to claim 6, wherein the one or more excipients is one or more of a binder, filler, lubricant, emulsifier, suspending agent, sweetener, flavoring, preservative, buffer, wetting agent, disintegrant, effervescent agent, additive, and mixtures thereof.
8. The composition according to claim 7, wherein the additive is selected from the group consisting of microcrystalline cellulose, lactose, sucrose, fructose, glucose, dextrose, dibasic calcium phosphate, calcium sulfate, cellulose, methylcellulose, cellulose derivatives, kaolin, mannitol, lactitol, maltitol, xylitol, sorbitol, sugar alcohols, dry starch, dextrin, maltodextrin, polysaccharides, and mixtures thereof.
9. The composition according to claim 6, further comprising one or more pharmaceutically acceptable carriers, pharmaceutically acceptable excipients, medicinal agents, pharmaceutical agents, adjuvants, diluents, and mixtures thereof.
10. A pharmaceutical or nutraceutical dosage form comprising the cocrystal according to claim 1.
11. The dosage form according to claim 10, wherein the dosage form is an oral dosage form selected from the group consisting of a tablet, capsule, powder, suspension and lozenge.
12. The dosage form according to claim 10, wherein the dosage form comprises a coated or uncoated tablet comprising one or more of a release modifying agent, glidant, compression aid, disintegrant, effervescent agent, lubricant, binder, diluent, flavor, flavor enhancer, sweetener, and preservative.
13. A method of making a pterostilbene:carbamazepine cocrystal comprising:
   adding a pre-determined amount of solid pterostilbene and solid carbamazepine in a vessel; and
   grinding the mixture for a pre-determined period of time.
14. The method according to claim 13, further comprising the step of adding a suitable solvent to the vessel.
15. The method according to claim 14, wherein the solvent is selected from one of chloroform, acetonitrile, ethanol, or p-dioxane.
16. A method of making a pterostilbene:carbamazepine cocrystal comprising:
   to a solution of pterostilbene dissolved in a suitable solvent, mixing an amount of carbamazepine for a pre-determined period of time, or to a solution of carbamazepine dissolved in a suitable solvent, mixing an amount of pterostilbene for a pre-determined period of time; and
   isolating the solids.
17. The method according to claim 16, wherein the step of isolating involves filtering the mixture.
18. The method according to claim 16, wherein the step of mixing is conducted at a temperature above room temperature.
19. The method according to claim 16, further comprising cooling the mixture before isolating the solid.

20. The method according to claim 16, where the suitable solvent is toluene.

21. A method of making a pterostilbene:carbamazepine cocrystal comprising:
- in a first vessel containing a suitable solvent, dissolving an amount of pterostilbene and an amount of carbamazepine;
- optionally agitating or heating the mixture for a pre-determined time period; and
- isolating the solids.

22. The method according to claim 21, wherein the suitable solvent is methanol.

23. The method according to claim 21, further comprising the step of:
- placing the first vessel inside a second vessel having a suitable antisolvent for a pre-determined period of time.

24. The method according to claim 23, wherein the suitable antisolvent is water.

* * * * *